US006075042A

United States Patent [19]

Latorse

[11] Patent Number: 6,075,042

[45] Date of Patent: Jun. 13, 2000

[54] FUNGICIDAL COMPOSITION COMPRISING A 2-IMIDAZOLIN-5-ONE

[75] Inventor: Marie-Pascale Latorse, Sourcieux les Mines, France

[73] Assignee: Rhone Poulenc Agrochimie, Lyon Cedex, France

[21] Appl. No.: 09/228,946

[22] Filed: Jan. 12, 1999

Related U.S. Application Data

[62] Division of application No. 08/776,064, filed as application No. PCT/FR95/00972, Jul. 20, 1995, Pat. No. 5,906,986.

[30] Foreign Application Priority Data

Jul. 22, 1994 [FR] France .................................. 94 09331

[51] Int. Cl.[7] .......................... A01N 37/12; A01N 37/34; A01N 37/44; A01N 43/50; A01N 43/76

[52] U.S. Cl. .......................... 514/376; 514/386; 514/528; 514/539

[58] Field of Search .................................... 514/386, 528, 514/376, 539

[56] References Cited

U.S. PATENT DOCUMENTS

| | | | |
|---|---|---|---|
| Re. 33,989 | 7/1992 | Wenderoth et al. | 514/522 |
| 4,829,085 | 5/1989 | Wenderoth et al. | 514/522 |

FOREIGN PATENT DOCUMENTS

| | | |
|---|---|---|
| 651021 | 7/1993 | Australia . |
| 0253213 | 1/1988 | European Pat. Off. . |
| 0398692 | 11/1990 | European Pat. Off. . |
| 0551048 | 7/1993 | European Pat. Off. . |
| 0578586 | 1/1994 | European Pat. Off. . |
| 0599749 | 6/1994 | European Pat. Off. . |
| 0629616 | 12/1994 | European Pat. Off. . |
| 93/24467 | 12/1993 | WIPO . |

OTHER PUBLICATIONS

Tammes, *Neth. J. Plant Path.* 70 (1964), pp. 73–80.

Limpel et al, Proc. NEWCC 16:48–53 (1962).

*The Pesticide Manual*, ed. Worthington et al, British Crop Protection Council, 9th edition, pp. 71–72, 124–125, 143–144, 145–146, 193–195, 229–231, 257–258, 268–269, 328–330, 351–352, 356–357, 380–382, 382–384, 428–429, 448–449, 474–475, 482–483, 510–511, 514–515, 518–519, 530–532, 562–563, 603–604, 635–636, 637–638, 660–661, 669–670, 689–690, 755–756, 832–833, 834–835, 942–943, 965–966, 1001–1003, 1019–1020, 1033–1034, 1041–1042 and 1048–1050.

*Index Phytosanitaire*, Association de Coordination Technique Agricole, 30th edition, 1994, pp. 156, 158.

*Primary Examiner*—Allen J. Robinson
*Attorney, Agent, or Firm*—Finnegan, Henderson, Farabow, Garrett & Dunner, L.L.P.

[57] ABSTRACT

A fungicidal composition comprising a compound A having the formula:

(I)

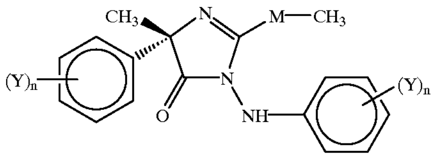

wherein M is an oxygen or sulphur atom, n is 0 or 1, and Y is a fluorine or chlorine atom or a methyl radical; and at least one fungicidal compound B. A method for preventing or controlling phytopathogenic fungi on crops by applying an effective and non-plant-poisonous amount of said compound on the exposed parts of the plants is also disclosed.

26 Claims, 29 Drawing Sheets

FUNGICIDAL COMPOSITION COMPRISING A 2-IMIDAZOLIN-5-ONE

This application is a divisional of copending U.S. application Ser. No. 08/776,064, filed May 6, 1997, now U.S. Pat. No. 5,906,986, which is the U.S. national stage of International Application No. PCT/FR95/00972, filed Jul. 20, 1995 and designating the U.S. application Ser. No. 08/776,064 is incorporated by reference herein in its entirety and relied upon.

The subject of the present invention is a fungicidal composition comprising a 2-imidazolin-5-one type compound and a process using the said composition and intended for protecting, curatively or preventively, crops against fungal attacks.

Racemic compounds derived from 2-imidazolin-5-ones with fungicidal action, which make it possible to prevent the growth and development of phytopathogenic fungi capable of attacking crops, are known especially through European Patent Application EP 551048.

It is however always desirable to enhance the activity spectrum and the efficacy of such compounds with fungicidal action.

It is also desirable to have available fungicidal products having a curative activity since in this case it is possible to decrease the number of systematic preventive treatments while ensuring good control of parasites.

It is also highly desirable to have available fungicidal products with lasting enhanced action such that the number of plant-protection treatments necessary for good control of parasites can be spaced out over time.

It is in all cases particularly advantageous to be able to decrease the quantity of chemical products spread in the environment while ensuring effective protection of crops against fungal attacks.

It has now been found that one (or several) of the preceding objectives could be achieved by means of the fungicidal composition according to the present invention.

The subject of the present invention is therefore, firstly, a fungicidal composition comprising a compound A of formula (I):

(I)

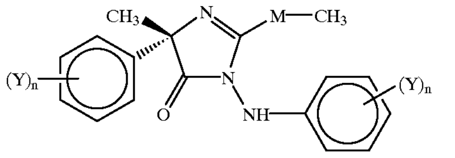

in which:

M represents an oxygen or sulphur atom;

n is an integer equal to 0 or 1;

Y is a fluorine or chlorine atom, or a methyl radical;

and at least one fungicidal compound B chosen from the group comprising:

- the derivatives of dithiocarbamic acid and its salts such as maneb, mancozeb, zineb, metiram-zinc,
- the derivatives of phosphorous acid such as metallic phosphites such as fosetyl-Al, phosphorous acid itself and its alkali metal or alkaline-earth metal salts,
- the chlorinated derivatives of benzene, such as chlorothalonil,
- the derivatives comprising a heterocycle containing from 1 to 2 nitrogen atoms such as fluazinam, fludioxonil, prochloraz,
- the derivatives of triazoles such as bromuconazole, cyproconazole, difenoconazole, diniconazole, epoxyconazole, fenbuconazole, flusilazole, flutriafol, hexaconazole, metconazole, tebuconazole, tetraconazole, triticonazole,
- the dicarboximide derivatives such as captan, folpel, captafol, iprodione, procymidone, vinchlozolin,
- copper or the organic or inorganic derivatives of copper, such as copper oxychloride or copper hydroxide,
- amides such as cymoxanil, metalaxyl, benalaxyl and oxadixyl,
- the derivatives of morpholine such as dimethomorph, dodemorph, tridemorph, fenpropimorph, fenpropidin, triadimenol,
- the derivatives of the methoxyacrylate type such as methyl-(E)-2-{2-[6-(2-cyanophenoxy)pyrimidin-4-yloxy]phenyl}-3-methoxyacrylate, methyl-(E)-methoxyimino[α-(o-tolyloxy)-o-tolyl]acetate, or alternatively N-methyl-(E)-methoxyimino[2-(2,5-dimethyl phenoxethyl)phenyl]acetamide,
- the derivatives of guanidine such as dodine,
- a derivative of the phenylbenzamide type of formula (II):

(II)

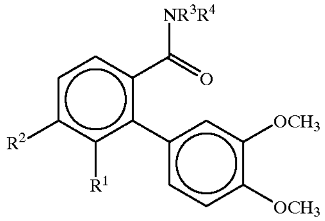

in which:

$R^1$ and $R^2$, which are identical or different, are a hydrogen or halogen atom, or an optionally halogenated alkyl radical, and $R^3$ and $R^4$, which are identical or different, are an alkyl radical of 1 to 4 carbon atoms.

Figure 1:
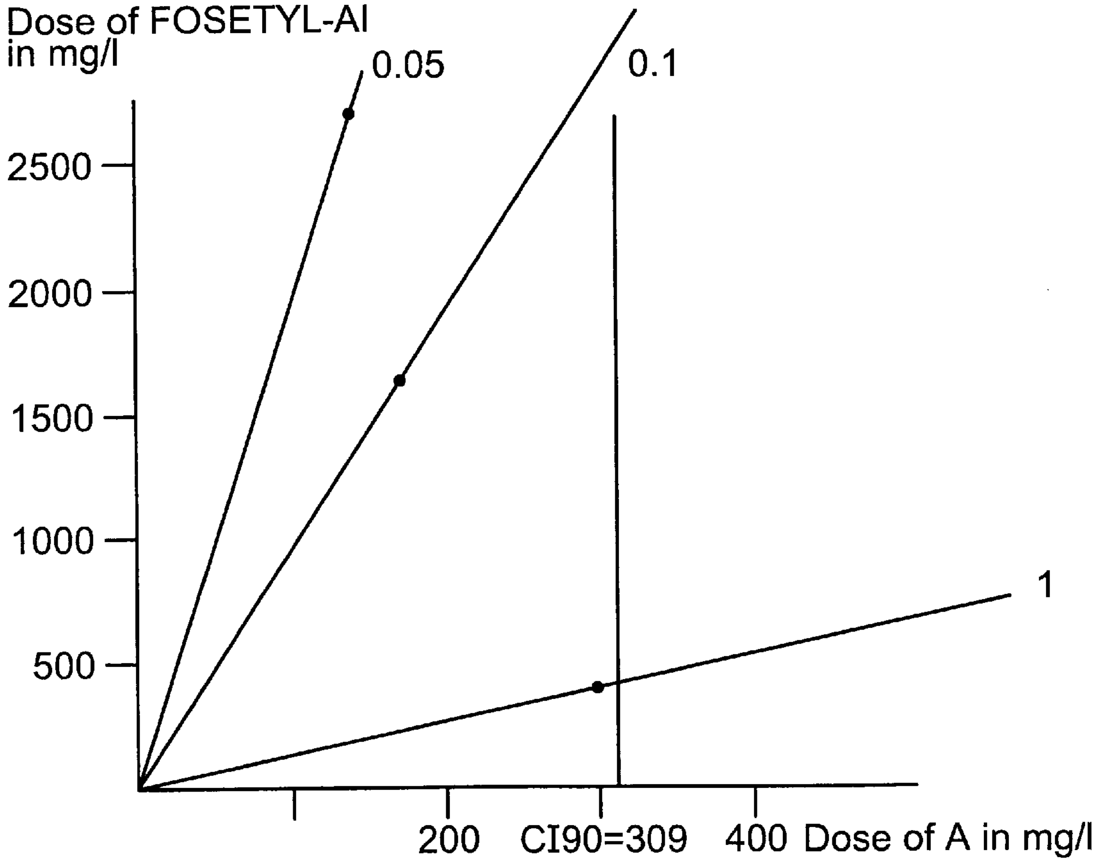
FIG. 1 is an $ED_{90}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and fosetyl-Al as compound B.

The fungicidal composition according to the invention advantageously comprises the components A and B in a weight ratio A/B of between 0.0005 and 50, preferably of between 0.001 and 10.

It is clearly understood that the said fungicidal composition may contain a single compound B or more than one such compound, for example 1, 2 or 3 B compounds depending on the use for which it is intended.

The fungicidal composition according to the invention for which compound A is the compound of formula (I) in which M is a sulphur atom and n is equal to 0, also called (4S)-4-methyl-2-methylthio-4-phenyl]-phenylamino-2-imidazolin-5-one is preferred.

One of the following derivatives is preferred for the meaning of compound B:

a derivative of dithiocarbamic acid and its salts chosen from maneb, mancozeb, metiram-zinc, a derivative of phosphorous acid chosen from fosetyl-Al, and phosphorous acid itself and its calcium or potassium salts, chlorothalonil, a derivative comprising a heterocycle containing from 1 to 2 nitrogen atoms chosen from fluazinam, fludioxonil, prochloraz, a triazole derivative chosen from bromuconazole, difenoconazole, epoxyconazole, tebuconazole, triticonazole, a dicarboximide derivative chosen from folpel or iprodione, a copper derivative chosen from copper oxychloride or copper hydroxide, an amide chosen from cymoxanil, metalaxyl or oxadixyl, dimethomorph, the derivative of the phenylbenzamide type which corresponds to the formula (I) in which $R^1$ represents a hydrogen atom, $R^2$ represents a trifluoromethyl radical, $R^3$ represents a methyl radical and $R^4$ represents an ethyl radical; in other words the derivative of the phenylbenzamide type called N-methyl-1N-ethyl-2-(3,4-dimethoxyphenyl)-4-trifluoromethylbenzamide.

Among the meanings more especially preferred for compound B which are defined above, fosetyl-Al, mancozeb, cymoxanil, dimethomorph, oxadixyl or N-methyl-N-ethyl-2-(3,4-dimethoxyphenyl)-4-trifluoromethylbenzamide is again preferred. Quite unexpectedly, the composition according to the invention thus considerably enhances the action of the active substances taken separately for a number of fungi which are particularly harmful for crops, such as in particular vine or solanaceous crops. This enhancement results especially in a decrease in the doses of each of the constituents, which is particularly advantageous for the user and the environment. The fungicidal product thus has synergistic properties confirmed by applying the Tammes method, “Isoboles, a graphic representation of synergism in pesticides” Netherlands Journal of Plant Pathology, 70 (1964), p. 73–80 or as defined by Limpel, L. E., P.H. Schuldt and D. Lammont, 1962, Proc. NEWCC 16: 48–53, using the following formula, also called Colby formula:

$$E=X+Y-X.Y/100$$

in which:

E is the expected percentage inhibition of the growth of the fungus by a mixture of two fungicides A and B at defined doses, equal to a and b respectively;

X is the observed percentage inhibition by fungicide A at dose a,

Y is the observed percentage inhibition by fungicide B at dose b.

When the observed percentage inhibition of the mixture is greater than E, there is synergy.

Preferably, when component B is a phosphorous acid derivative, and is especially fosetyl-Al, the A/B ratio is between 0.001 and 2, preferably between 0.002 and 1.

Preferably, when component B is a derivative of formula (II), and is especially N-methyl-N-ethyl-2-(3,4-dimethoxyphenyl)-4-trifluoromethylbenzamide, the A/B ratio is between 0.1 and 10, preferably between 0.2 and 10, and still more preferably between 0.25 and 4.

Preferably, when component B is cymoxanil, the A/B ratio is between 0.05 and 4, preferably between 0.2 and 4, and still more preferably between 0.25 and 4.

Preferably, when component B is oxadixyl, the A/B ratio is between 0.5 and 30, preferably between 0.5 and 10.

Preferably, when component B is a dithiocarbamic acid derivative such as mancozeb, the A/B ratio is between 0.02 and 2, preferably between 0.1 and 1.

Preferably, when component B is a morpholine derivative and especially dimethomorph, the A/B ratio is between 0.1 and 2, preferably between 0.2 and 1.

Compound A is described in European Patent Application No. 94420167.2 which was unpublished on the filing date of the present patent application.

The compound A of formula (I) in which M is a sulphur atom and n is equal to 0, in other words (4S)-4-methyl-2-methylthio-4-phenyl-1-phenylamino-2-imidazolin-5-one, can be prepared in the following manner.

Preparation of (4S)-4-methyl-2-methylthio-4-phenyl-1-phenylamino-2-imidazolin-5-one:

This preparation is carried out in two stages.

First stage:

In a first stage, methyl (2S)-2-isothiocyanato-2-phenylpropionate is first prepared according to one of the procedures mentioned in Sulfur Reports Volume 8 (5) pages 327–375 (1989), from the corresponding amino ester which is itself easily obtained from the α-amino acid.

Thus, 780 g (3.61 moles) of (+)-[methyl (2S)-2-amino-2-phenylpropionate hydrochloride] are introduced into a 20-l reactor, followed by 3.4 l of water. The temperature is adjusted to 20° C. 3.4 l of toluene are added and then 911 g (10.8 moles) of sodium hydrogen carbonate are added in fractions over 1 hour. The temperature decreases to 8–9° C. 276 ml (3.61 moles) of thiophosgene are poured in over 2 hours. The reaction is accompanied by a gaseous emission and a rise in temperature which reaches 24° C. at the end of the pouring in. The medium is again maintained stirring for 2 hours. After decantation, the aqueous phase is extracted with 2 l of toluene. The combined toluene phases are washed with 4 l of water and then dried over magnesium sulphate. The solution is concentrated under reduced pressure.

682 g of (+)-[methyl (2S)-2-isothiocyanato-2-phenylpropionate] are thus obtained in the form of a slightly coloured oil (yield=85%).

A specific rotation, equal to +16° (+ or −6.4°), is measured according to the usual method and for a solution of 0.78 g of product in 100 ml of chloroform, at a temperature of 29° C.

Second stage:

In a second stage, 682 g (3.08 moles) of methyl (2S)-2-phenyl-2-isothiocyanatopropionate, prepared in the manner which has just been described, are dissolved in 4 l of anhydrous tetrahydrofuran and then introduced into a 20-l reactor through which runs an argon stream. The whole is cooled to 15° C. 343 g (3.08 moles) of phenylhydrazine, dissolved in 2 l of tetrahydrofuran, are poured in over 30 min while the temperature is maintained between 15° C. and 18° C. The medium is maintained stirring for 40 min and then cooled to 0°. A solution of 346 g (3.08 moles) of potassium tertbutoxide is poured into 4 l of tetrahydrofuran over 1 hour while the temperature is maintained at 0° C. The stirring of the medium in continued for 2 hours at 0° C. and the formation of a light pink precipitate is observed. 218 ml (3.39 moles) of methyl iodide are poured in over 15 min while the temperature is maintained between 0° C. and 3° C. then the temperature is allowed to rise to room temperature while the stirring is maintained for 2 hours. The reaction mixture is poured over 5 l of water. After decantation, the aqueous phase is extracted with three times 3 l of ethyl acetate. The combined organic phases are washed with 5 l of water, dried over magnesium sulphate then concentrated under reduced pressure. 1,099 g of a brown solid are obtained. The latter is recrystallized from 2 l of toluene.

After drying, 555 g of (+)-(4S)-4-methyl-2-methylthio-4-phenyl-1-phenylamino-2-imidazolin-5-one are obtained in the form of an off-white solid melting at 138° C. (yield a 58%).

A specific rotation equal to +61.1° (+ or −2.9°) is measured according to the usual method and for a solution of 0.86 g of product in 100 ml of ethanol, at 27° C.

An enantiomeric excess (e.e) greater than 98% is measured by high-performance liquid chromatography on a chiral phase.

The compound A of formula (I) in which M is an oxygen atom and n is equal to 0 in obtained by reacting (4S)-4-methyl-2-methylthio-4-phenyl-1-phenylamino-2-imidazolin-5-one with methanol and in the presence of sodium, according to a procedure described in Patent Application EP 599749.

The compound A of formula (I) in which n is equal to 1 is obtained from the embodiments indicated above with modifications of the starting reagents which are easily within the means of persons skilled in the art.

The structures corresponding to the common names of the fungicidal active substances appearing in the definition of B are indicated in at least one of the following two books:

"The pesticide manual" edited by Charles R. Worthing and Raymond J. Hance and published by the British Crop Protection Council, 9th Edition;

Index phytosanitaire 1994, published by the Association de Coordination Technique Agricole, 30th Edition.

As regards the methoxyacrylate type derivatives, methyl-(E)-2-{2-[6-(2-cyano-phenoxy)pyrimidin-4-yloxy]phenyl}-3-methoxyacrylate is described in International Application WO 9,208,703; methyl-(E)-methoxyimino[α-(o-tolyloxy)-o-tolyl]acetate is described in European Patent Application EP 253213; N-methyl-(E)-methoxyimino[2-(2,5-dimethylphenoxymethyl)phenyl]acetamide is described in European Patent Application EP 398692.

The phenylbenzamide type derivative is described in European Patent Application EP 0,578,586 published on Jan. 12, 1994.

The fungicidal composition according to the invention comprises, as active substance, compound A and at least one compound B in the form of a mixture with solid or liquid carriers which are agriculturally acceptable, and surface-active agents which are also agriculturally acceptable. In particular, inert and customary carriers and customary surface-active agents can be used. These compositions include not only compositions ready to be applied to the crop to be treated by means of an appropriate device, such as a spraying device, but also, commercially available concentrated compositions which must be diluted before application to the crop. Active substance designates the combination of compound A with at least one compound B.

These compositions may also contain all sorts of other ingredients such as, for example, protective colloids, adhesives, thickeners, thixotropic agents, penetrating agents, stabilizers, sequestrants and the like. More generally, compounds A and B may be combined with all solid or liquid additives corresponding to the usual formulation techniques.

Generally, the compositions according to the invention usually contain from 0.05 to 95% (by weight) of active substance, one or more solid or liquid carriers and, optionally, one or more surface-active agents.

The term "carrier", in the present text, designates a natural or synthetic organic or inorganic substance with which the active substance is combined to facilitate its application to the aerial parts of the plant. This carrier is therefore generally inert and must be agriculturally acceptable, especially on the treated plant. The carrier may be solid (clays, natural or synthetic silicates, silica, resins, waxes, solid fertilizers and the like) or liquid (water, alcohols, especially butanol and the like).

The surface-active agent may be an emulsifier, dispersing or wetting agent of the ionic or nonionic type or a mixture of such surface-active agents. There may be mentioned for example polyacrylic acid salts, lignosulphonic acid salts, phenolsulphonic or naphthalenesulphonic acid salts, polycondensates of ethylene oxide with fatty alcohols or fatty acids or fatty amines, substituted phenols (alkylphenols or arylphenols in particular), ester salts of sulphosuccinic acids, taurine derivatives (alkyltaurates in particular), phosphoric esters of alcohols or of polyoxyethylated phenols, esters of fatty acids and of polyols, derivatives containing sulphate, sulphonate and phosphate functional groups of the preceding compounds. The presence of at least one surface-active agent is generally essential when the active substance and/or inert carrier are insoluble in water and when the vector agent for the application is water.

Consequently, the compositions for agricultural use according to the invention may contain the active substance within very wide limits, ranging from 0.05% to 95% (by weight). Their content of surface-active agent is advantageously between 5% and 40% by weight.

These compositions according to the invention are themselves in fairly diverse, solid or liquid, forms.

As solid composition forms, there may be mentioned powders for dusting (with an active substance content which may be as high as 100%) and granules, especially those obtained by extrusion, by compacting, by impregnation of a granulated carrier or by granulation from a powder (the active substance content in these granules being between 0.5 and 80% for these latter cases), effervescent tablets or lozenges.

The fungicidal composition according to the invention may furthermore be used in the form of powders for dusting; a composition comprising 50 g of active substance and 950 g of talc may also be used; a composition comprising 20 g of active substance, 10 g of finely divided silica and 970 g of talc may also be used; these constituents are mixed and ground and the mixture is applied by dusting.

As liquid composition forms or forms intended to constitute liquid compositions during application, there may be mentioned solutions, in particular water-soluble concentrates, emulsifiable concentrates, emulsions, concentrated suspensions, aerosols, wettable powders (or powder for spraying), pastes and gels.

The emulsifiable or soluble concentrates most often comprise 10 to 80% of active substance, the emulsions or solutions ready for application containing, for their part, 0.001 to 20% of active substance.

In addition to the solvent, the emulsifiable concentrates may contain, when necessary, 2 to 20% of appropriate additives such as the stabilizers, surface-active agents, penetrating agents, corrosion inhibitors, colourings or adhesives previously mentioned.

From these concentrates, emulsions of any desired concentration, which are particularly suitable for application to the crops, may be obtained by dilution with water.

By way of example, here is the composition of some emulsifiable concentrates:

EXAMPLE EC 1 active substance 400 g/l alkali metal dodecylbenzenesulphonate 24 g/l oxyethylated nonylphenol containing 10 molecules of ethylene oxide 16 g/l cyclohexanone 200 g/l aromatic solvent qs 1 liter According to another emulsifiable concentrate formula, the following is used:

EXAMPLE EC 2 active substance 250 g epoxydized vegetable oil 25 g mixture of alkylarylsulphonate and polyglycol ether and fatty alcohols 100 g dimethylformamide 50 g xylene 575 g The concentrated suspensions, which can also be applied by spraying, are prepared so as to obtain a stable free-flowing product which does not settle and they usually contain from 10 to 75% of active substance, from 0.5 to 15% of surface-active agents, from 0.1 to 10% of thixotropic agents, from 0 to 10% of appropriate additives such as antifoams, corrosion inhibitors, stabilizers, penetrating agents and adhesives and, as carrier, water or an organic liquid in which the active substance is poorly soluble or insoluble: some organic solid substances or inorganic salts may be dissolved in the carrier to help prevent sedimentation or as antifreeze for the water.

By way of example, there is a composition of a concentrated suspension:

EXAMPLE CS 1 active substance 500 g polyethoxylated tristyrylphenol phosphate 50 g polyethoxylated alkylphenol 50 g sodium polycarboxylate 20 g ethylene glycol 50 g organopolysiloxane oil (antifoam) 1 g polysaccharide 1.5 g water 316.5 g The wettable powders (or powder for spraying) are usually prepared so that they contain 20 to 95% of active substance, and they usually contain, in addition to the solid carrier, from 0 to 30% of a wetting agent, from 3 to 20% of a dispersing agent, and, when necessary, from 0.1 to 10% of one or more stabilizers and/or other additives, such as penetrating agents, adhesives, or anticaking agents, colourings and the like.

In order to obtain the powders for spraying or wettable powders, the active substances are intimately mixed in the appropriate mixers with the additional substances and ground using mills or other appropriate grinders. Powders for spraying are thereby obtained whose wettability and capacity to form suspensions are advantageous; they can be suspended with water at any desired concentration and these suspensions can be used very advantageously in particular for application to plant leaves.

In place of wettable powders, pastes can be made. The conditions and methods of preparing and using these pastes are similar to those of wettable powders or powders for spraying.

By way of example, here are various compositions of wettable powders (or powders for spraying):

EXAMPLE WP 1 active substance 50% ethoxylated fatty alcohol (wetting agent) 2.5% ethoxylated phenylethylphenol (dispersing agent 5% chalk (inert carrier) 42.5%

EXAMPLE WP 2 active substance 10%

$C_{13}$ branched-type oxo synthetic alcohol ethoxylated by 8 to 10 ethylene oxides 0.75% (wetting agent)

neutral calcium lignosulphonate (dispersing 12% agent)

calcium carbonate (inert gs 100% filler)

EXAMPLE WP 3

This wettable powder contains the same ingredients as in the preceding example, in the proportions below:

active substance 75% wetting agent 1.50% dispersing agent 8% calcium carbonate (inert qs 100% filler)

EXAMPLE WP 4 active substance 90% ethoxylated fatty alcohol (wetting agent) 4% ethoxylated phenylethylphenol (dispersing agent) 6%

EXAMPLE WP 5 active substance 50% mixture of anionic and nonionic surfactants (wetting agent) 2.5% sodium lignosulphonate (dispersing agent) 5% kaolinic clay (inert carrier) 42.5%

The aqueous dispersions and emulsions, for example the compositions obtained by diluting a wettable powder or an emulsifiable concentrate according to the invention with water, are included within the general scope of the present invention. The emulsions may be of the water-in-oil or oil-in-water type and they may have a thick consistency like that of a "mayonnaise".

The fungicidal compositions according to the is invention may be formulated in the form of water-dispersible granules which are also included within the scope of the invention.

These dispersible granules, with an apparent density generally of between about 0.3 and 0.6 have a particle size generally of between about 150 and 2,000 and preferably between 300 and 1,500 microns.

The active substance content of these granules is generally between about 1% and 90%, and preferably between 25% and 90%.

The rest of the granule is essentially composed of a solid filler and optionally of surface-active adjuvants which confer water-dispersibility properties on the granule. These granules may be essentially of two distinct types depending on whether the chosen filler is soluble in water or otherwise. When the filler is water-soluble, it may be an inorganic or preferably an organic filler. Excellent results are obtained with urea. In the case of an insoluble filler, the latter is preferably an inorganic filler such as for example kaolin or bentonite. It is, in this case, advantageously accompanied by surface-active agents (in an amount of 2 to 20% by weight of the granule) of which more than half for example consists of at least one, essentially anionic, dispersing agent such as an alkali metal or alkaline-earth metal polynaphthalenesulphonate or an alkali metal or alkaline-earth metal lignosulphonate, the rest consisting of nonionic or anionic wetting agents such as an alkali metal or alkaline-earth metal alkylnaphthalenesulphonate.

Moreover, although this is not essential, other adjuvants such as antifoaming agents may be added.

The granule according to the invention may be prepared by mixing the necessary ingredients followed by granulation by means of several techniques which are known per se (coating device, fluidized bed, atomizer, extrusion, and the like). The procedure generally ends with crushing followed by sieving to the chosen particle size within the limits mentioned above. It is also possible to use granules obtained as above and then impregnated with a composition containing the active substance.

Preferably, it is obtained by extrusion, the procedure being carried out as indicated in the examples below.

EXAMPLE DG1

Dispersible Granules

90% by weight of active substance and 10% of pearl urea are mixed in a mixer. The mixture is then ground in a toothed roll crusher. A powder is obtained which is moistened with about 8% by weight of water. The wet powder is extruded in a perforated roll extruder. A granule is obtained which is dried, then crushed and sieved, so that only granules with a size of between 150 and 2,000 microns are kept respectively.

EXAMPLE DG2

Dispersible Granules

The following constituents are mixed in a mixer:

active substance 75% wetting agent (sodium alkylnaphthalenesulphonate) 2% dispersing agent (sodium polynaphthalenesulphonate) 8% water-insoluble inert filler (kaolin) 15%

This mixture in granulated in a fluidized bed, in the presence of water, and then dried, crushed and sieved so as to obtain granules with a size of between 0.15 and 0.80 mm.

These granules may be used alone, dissolved or dispersed in water so as to obtain the desired dose. They may also be used to prepare combinations with other active substances, especially fungicides, the latter being in the form of wettable powders, or granules or aqueous suspensions.

As regards the compositions suitable for storage and for transport, they contain more advantageously from 0.5 to 95% (by weight) of active substance.

The subject of the invention is finally a process for controlling, curatively or preventively, phytopathogenic crop fungi, characterized in that an effective and nonphytotoxic quantity of a fungicidal composition according to the invention is applied to the aerial parts of the plants.

The phytopathogenic crop fungi which can be controlled by this process are especially those:

of the Oomycetes group:

of the genus Phytophthora such as *Phytophthora infestans* (blight of solanaceous crops, especially potato or tomato blight), *Phytophthora citrophthora, Phytophthora capsici, Phytophthora cactorum, Phytophthora palmvora, Phytophthora cinnamoni, Phytophthora megasperma, Phytophthora parasitica,* of the Peronosporaceae family, especially *Plasmopara viticola* (vine downy mildew), *Plasmopara halstedei* (sunflower downy mildew), Pseudoperonospora sp (especially cucurbit and hop downy mildew), *Bremia lactucae* (lettuce downy mildew), *Peronospora tabacinae* (tobacco downy mildew), of the Adelomycetes group:

of the genus Alternaria, for example *Alternaria solani* (solanaceous crop, especially tomato and potato diseases caused by Alternaria), of the genus Guignardia, especially *Guignardia bidwelli* (black rot of the vine), of the genus Oidium, for example vine powdery mildew (*Uncinula necator*); powdery mildew of leguminous crops, for example *Erysiphe polygoni* (crucifer powdery mildew); *Leveillula taurica, Erysiphe cichoracearum, Sphaerotheca fuligena;* (powdery mildew of Cucurbitaceae, of compositae, of tomato); *Erysiphe communis* (beet and cabbage powdery mildew); *Erysiphe pisi* (pea and lucerne powdery mildew); *Erysiphe polyphaga* (bean and cucumber powdery mildew); *Erysiphe umbelliferarum* (powdery mildew of unmbellifers, especially of carrot); *Sphaerotheca humuli* (hop powdery mildew); *Erysiphe giaminis* (cereal powdery mildew);

of the genus Septoria, for example *Septoria nodorum* or *Septoria tritici* (septoria spot of cereals);

of the Basidiomycetes group:

of the genus Puccinia, for example *Puccinia recondita* or *striiformis* (wheat rust).

The fungicidal composition which is the subject of the invention is applied by means of various methods of treatment such as:

spraying a liquid comprising the said composition onto the aerial parts of the crops to be treated, dusting, incorporation of granules or powders into soil, sprinkling, injection into trees or daubing.

The spraying of a liquid onto the aerial parts of the crops to be treated is the preferred method of treatment.

"Effective or nonphytotoxic quantity" is understood to mean a quantity of composition according to the invention which is sufficient to allow the control and the destruction of the fungi present or which may appear on the crops, and not causing any symptoms of phytotoxicity for the said crops. Such a quantity may vary within wide limits depending on the fungus to be controlled, the type of crop, the climatic conditions and the nature of the compound B included in the fungicidal composition according to the invention. This quantity may be determined by systematic field trials within the capability of persons skilled in the art.

Under the usual conditions of agricultural practice, the doses of fungicidal composition according to the invention per volume of liquid for spraying ranging from 1 g/hl to 500 g/hl, corresponding essentially to doses per hectare of between 10 g/ha and 5,000 g/ha generally give good results.

The following examples are given purely to illustrate the invention which they do not limit in any manner.

In these examples, the compound A used is (4S)-4-methyl-2-methylthio-4-phenyl-1-phenylamino-2-imidazolin-5-one.

In the figures accompanying the present text, the dose of each active substance taken separately, required for the control of phytopathogenic fungus at the indicated level, is compared with that of the 2 active substances taken in the form of a mixture. The effective dose of each active substance taken separately is indicated on the x-axis and on the y-axis and a straight line is drawn which cuts across these 2 axes and links these 2 doses. While an active substance taken separately is not effective (for example fosetyl-Al in FIG. 1) the straight line is parallel to the coordinate axis which indicates the doses of this active substance. As regards the 2 active substances taken in the form of a mixture, the dose of the mixture in a given ratio is indicated by a dot. A straight line is drawn between this dot and the origin of the system of axes, such that the ratio of active substances may be conveniently indicated for each ratio tested.

Example 1: in vivo trial of the combination of A with fosetyl-Al on *Phytophthora infestans* (tomato blight) by preventive treatment at 48 hours A 60 mg suspension is prepared comprising compounds A and B in a liquid mixture consisting of 0.3 ml of a surface-active agent (oleate of a polyoxyethylenated derivative of sorbitan) diluted 10% in water and of 60 ml of water.

Component B is fosetyl-Al; the A/B ratio is 0.05–0.1–1.

Tomato plants (Marmande variety) are cultivated in pots. When these plants are one month old (5 to 6-leaf stage, height 12 to 15 cm), they are treated by spraying the above suspension.

At the end of 48 hours, each plant is contaminated by spraying using an aqueous suspension of Phytophthora infestans spores (30,000 sp/$cm^3$).

After this contamination, the tomato plants are incubated for 7 days at about 20° C. in an atmosphere saturated with moisture.

The reading is made 7 days after the contamination, in comparison with the control plants.

The results obtained are presented in the form of points, corresponding to 90% destruction of the pest and are placed in a Tammes diagram which comprises, on the x-axis, the doses of A expressed in mg/l and on the y-axis the doses of B also in mg/l.

The diagram of FIG. 1 is obtained in which it appears that fosetyl-Al, when it is applied alone, is not effective under the trial conditions. It appears, nevertheless, that the addition of fosetyl-Al makes it possible, quite unexpectedly, to decrease the dose of A necessary for the destruction of 90% of the pest below 309 mg/l which corresponds to the dose of A alone which it is necessary to apply in order to obtain the same percentage destruction.

The arrangement of the points which is obtained therefore indicates an effect termed, according to the Tammes method mentioned above, "one-sided effect". This arrangement corresponds to a type II isobole according to the said method (page 74 of the corresponding bibliographic reference already mentioned) and is characteristic of a synergy.

Example 2: In vivo trials of the combination of A with fosetyl-Al on *Plasmopara viticola* (vine downy mildew) by preventive treatment at 72 hours A 60 mg suspension is prepared comprising compounds A and B in a liquid mixture consisting of 0.3 ml of a surface-active agent (oleate of a polyoxyethylenated derivative of sorbitan) diluted 10% in water and of 60 ml of water.

Component B is fosetyl-Al; the A/B ratio is 0.002–0.004–0.02.

Vine cuttings (*Vitis vinifera*) Chardonnay variety, are cultivated in pots. When these plants are 2 months old (8 to 10-leaf stage, height 10 to 15 cm), they are treated by spraying using the above suspension.

Plants used as controls are treated with a similar suspension but not containing any active substance (formulation blank).

After drying for 72 hours, each plant is contaminated by spraying an aqueous *Plasmopara viticola* spore suspension obtained from sporulated leaves contaminated 7 days earlier. These spores are suspended in an amount of 100,000 units per $cm^3$.

The contaminated plants are then incubated for two days at about 18° C., in an atmosphere saturated with moisture, and then for 5 days at 20–22° C. under a relative humidity of 90–100%.

The reading is made 7 days after the contamination, In comparison with the control plants.

The results obtained are presented in the form of points, corresponding to 90% destruction of the pest and are placed in a Tammes isobole diagram which has, on the x-axis, the doses of A expressed in mg/l and on the y-axis the doses of B also in mg/l.

Figure 2:
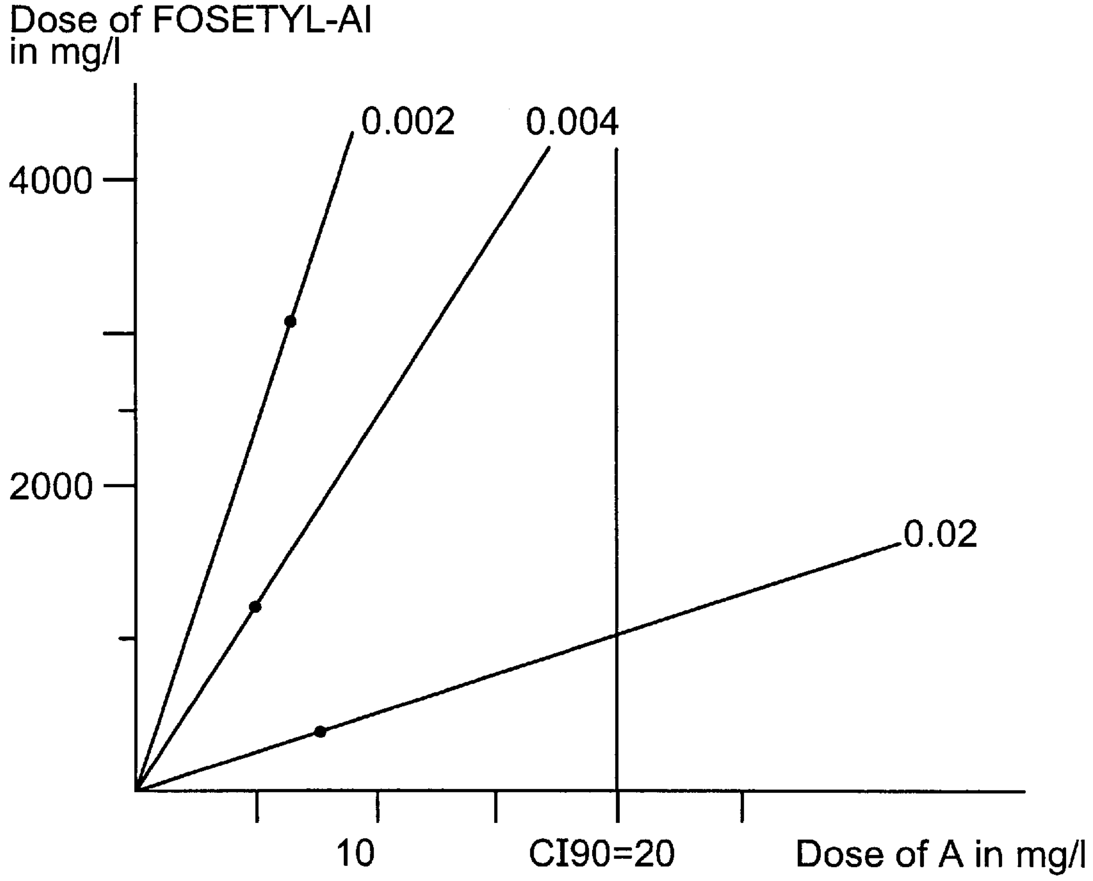
FIG. 2 is an $ED_{90}$ Tammes isobole plot for preventive control of *Plasmopara viticola* in Chardonnay vine plants based on testing of combinations of (4S)-4-methyl-2-methylthio-4-phenyl-1-phenylamino-2-imidazolin-5-one as compound A and fosetyl-Al as compound B.

The diagram of FIG. 2 is obtained in which it appears that fosetyl-Al, when it is applied alone, is not effective under the trial conditions. It appears, nevertheless, that the addition of fosetyl-Al makes it possible, quite unexpectedly, to decrease the dose of A necessary for the destruction of 90% of the pest below 20 mg/l, which corresponds to the dose of A alone which it is necessary to apply in order to obtain the same percentage destruction.

The arrangement of the points which is obtained therefore indicates an effect termed according to the Tammes method mentioned above "one-sided effect". This arrangement corresponds to a type II isobole according to the said method (page 74 of the corresponding bibliographic reference already mentioned) and is characteristic of a synergy.

Example 3: In vivo trial of the combination of A with mancozeb on *Plasmopara viticola* (vine downy mildew) by preventive treatment at 24 hours Example 2 is repeated using as component B mancozeb, using A and B concentrations in the suspension for treating the plants equal to 3.2 and 12.5 mg/l respectively, and finally carrying out the contamination 24 hours after the treatment.

The efficacy measured, as well as the efficacy of products A and B alone measured under the same conditions, is indicated in the table below.

| | Dose (in mg/l) | Efficacy (in %) |
|---|---|---|
| Compound A | 3.2 | 80.8 |
| Mancozeb | 12.5 | 0 |
| Compound A + mancozeb | 3.2 + 12.5 | 90.4 |

Example 4: In vivo trial of the combination of A with cymoxanil on *Phytophthora infestans* (tomato blight) by preventive treatment at 48 hours Example 1 is repeated using as component B cymoxanil, using A/B ratios in the suspension for treating plants equal to 0.25–0.5–2–4.

Figure 3:
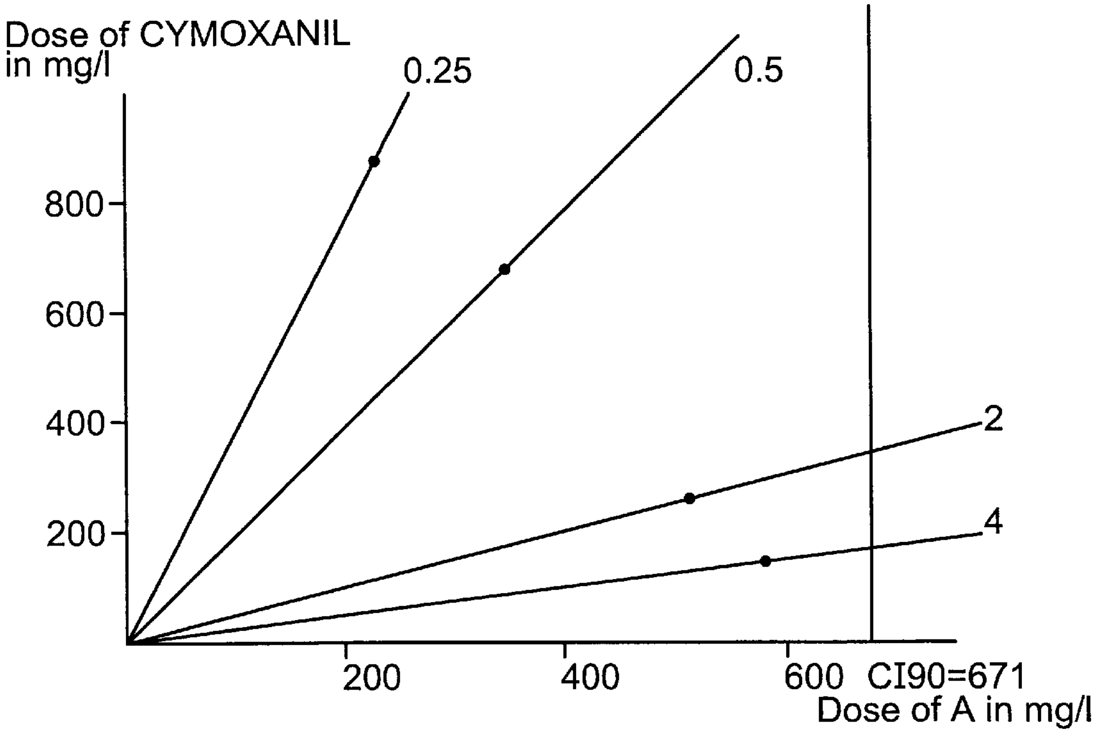
FIG. 3 is an $ED_{90}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and cymoxanil as compound B.

The diagram of FIG. 3 is obtained which shows an arrangement of the points similar to Example 1, which is characteristic of a synergy.

Example 5: In vivo trial of the combination of A with N-methyl-N-ethyl-2-(3,4-dimethoxyphenyl)-4-trifluoromethylbenzamide on *Phytophthora infestans* (tomato blight) by preventive treatment at 48 hours Example 1 is repeated using as component B N-methyl-N-ethyl-2-(3,4-dimethoxyphenyl)-4-trifluoromethylbenzamide, and using A/B ratios in the suspension for treating plants equal to 0.25–0.5–1–2–4.

The results obtained are presented in the form of points, corresponding to 90% destruction of the pest and are placed in a Tammes diagram which comprises, on the x-axis, the doses of A expressed in mg/l and on the y-axis the doses of B also in mg/l.

Figure 4:
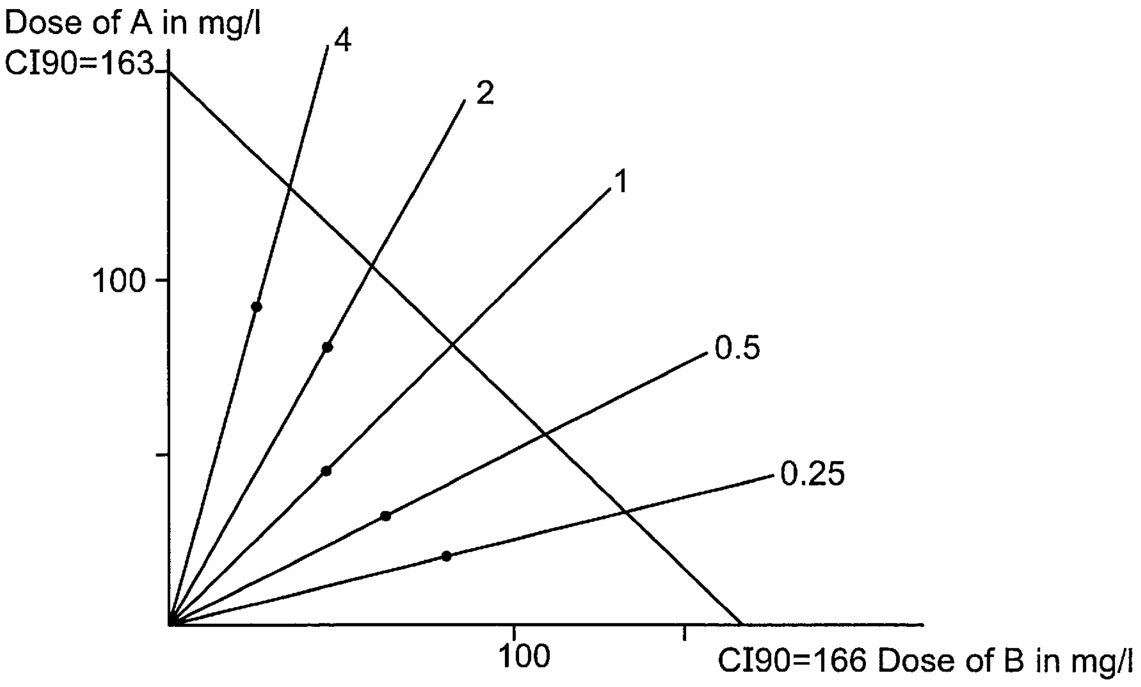
FIG. 4 is an $ED_{90}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and N-methyl-N-ethyl-2-(3,4-dimethoxyphenyl)-4-trifluoromethylbenzamide as compound B.

The diagram of FIG. 4 is obtained in which it appears that the addition of a dose of A of less than 163 mg/l (which corresponds to the dose of A alone which it is necessary to apply in order to obtain the destruction of 90% of the pest) makes it possible, quite unexpectedly, to decrease the dose of B necessary for the destruction of 90% of the pest below 166 mg/l (this value corresponding to the dose of B alone which it is necessary to apply in order to obtain the same percentage of destruction).

The arrangement of the points which is obtained therefore indicates an effect termed according to the Tammes method mentioned above "two-sided effect". This arrangement corresponds to a type III isobole according to the said method (page 75 of the corresponding bibliographic reference already mentioned) and is characteristic of a synergy.

Example 6: In vivo trial of the combination of A with dimethomorph on *Phytophthora infestans* (tomato blight) by preventive treatment at 48 hours Example 1 is repeated using as component B dimethomorph, and using A/B ratios in the suspension for treating plants equal to 0.25–0.5–1.

Figure 5:
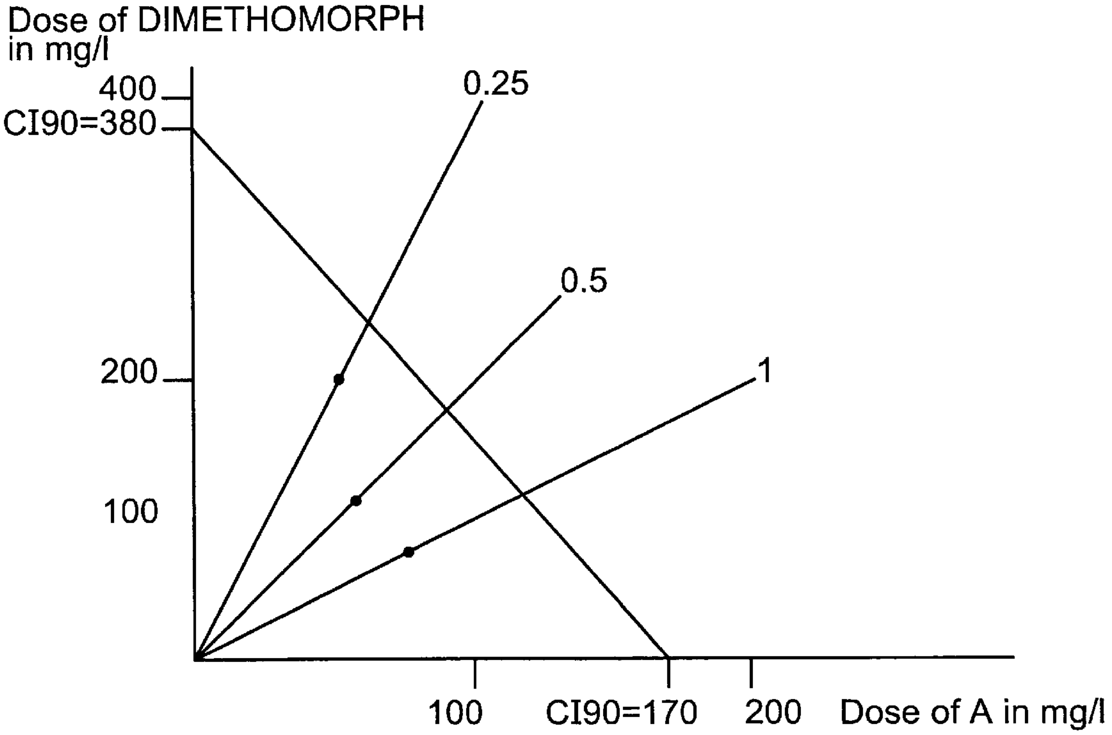
FIG. 5 is an $ED_{90}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and dimethomorph as compound B.

The diagram of FIG. 5 is obtained in which the arrangement of the points is similar to that obtained for Example 5 and is characteristic of a synergy.

Example 7: In vivo trial of the combination of A with oxadixyl on *Plasmopara viticola* (vine downy mildew, strain sensitive to phenylamides) by curative treatment at 48 hours A 60 mg suspension is prepared comprising compounds A and B in a liquid mixture consisting of 0.3 ml of a surface-active agent (oleate of a polyoxyethylenated derivative of sorbitan) diluted 10% in water and of 60 ml of water.

Component B is oxadixyl; the A/B ratio is 0.5–1–2–4.

Vine cuttings (*Vitis vinifera*), Chardonnay variety, are cultivated in pots. When these plants are 2 months old (8 to 10-leaf stage, height 10 to 15 cm), they are contaminated by spraying an aqueous *Plasmopara viticola* spore suspension obtained from sporulated leaves contaminated 7 days earlier. These spores are suspended In an amount of 100,000 units per $cm^3$.

The contaminated plants are then treated 48 hours after contamination by spraying using the suspension of fungicidal product prepared above.

Plants used as controls are treated with a similar suspension but not containing any active substance (formulation blank).

The plants contaminated, then treated are then incubated for two days at about 18° C. in an atmosphere saturated with moisture and then for 5 days at 20–22° C. under a relative humidity of 90–100%.

The reading is made 7 days after the contamination, in comparison with the control plants.

The results obtained are presented in the form of points, corresponding to 70% destruction of the pest and are placed in a Tammes isobole diagram which comprises, on the x-axis, the doses of A expressed in mg/l and on the y-axis the doses of B also in mg/l.

Figure 6:
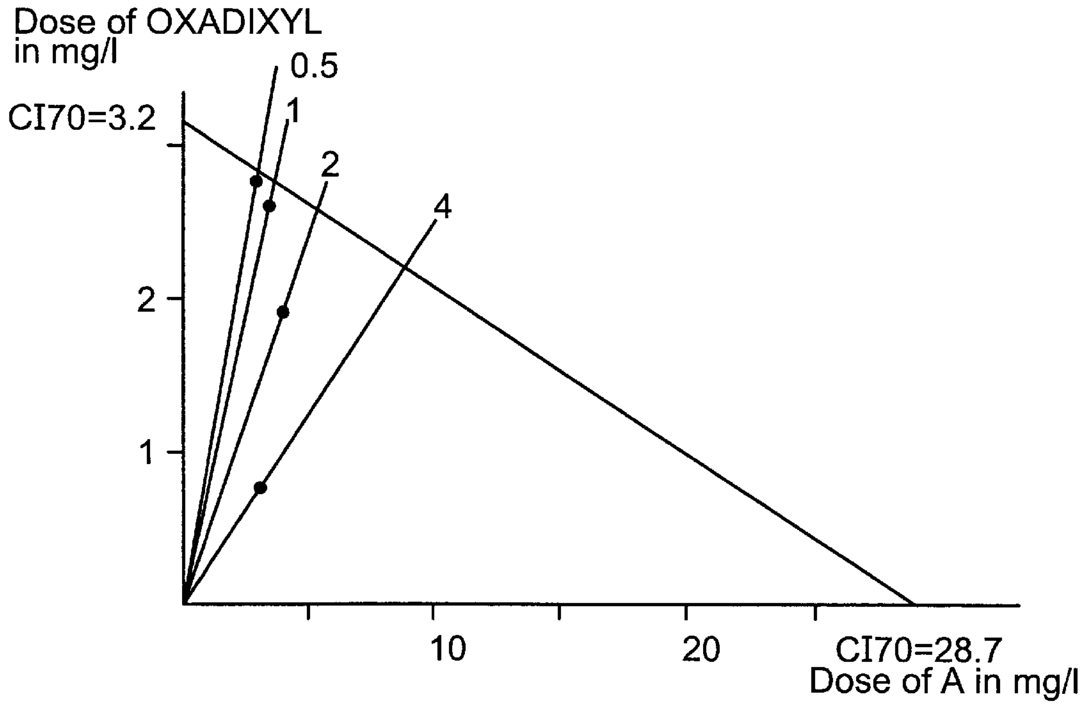
FIG. 6 is an $ED_{70}$ Tammes isobole plot for curative control of *Plasmopara viticola* in Chardonnay vine plants based on testing of combinations of (4S)-4-methyl-2-methylthio-4-phenyl-1-phenylamino-2-imidazolin-5-one as compound A and oxadixyl as compound B.

The diagram of FIG. 6 is obtained in which the arrangement of the points is similar to that obtained for Example 5 and is characteristic of a synergy.

Example 8: In vivo trial of the combination of A with chlorothalonil on *Phytophthora infestans* (tomato blight) by preventive treatment at 48 hours Example 1 is repeated using as compound B chlorothalonil; the A/B ratio is 0.125–0.25–0.5–1–2. The results corresponding to 70% destruction of the pest are presented.

Figure 7:
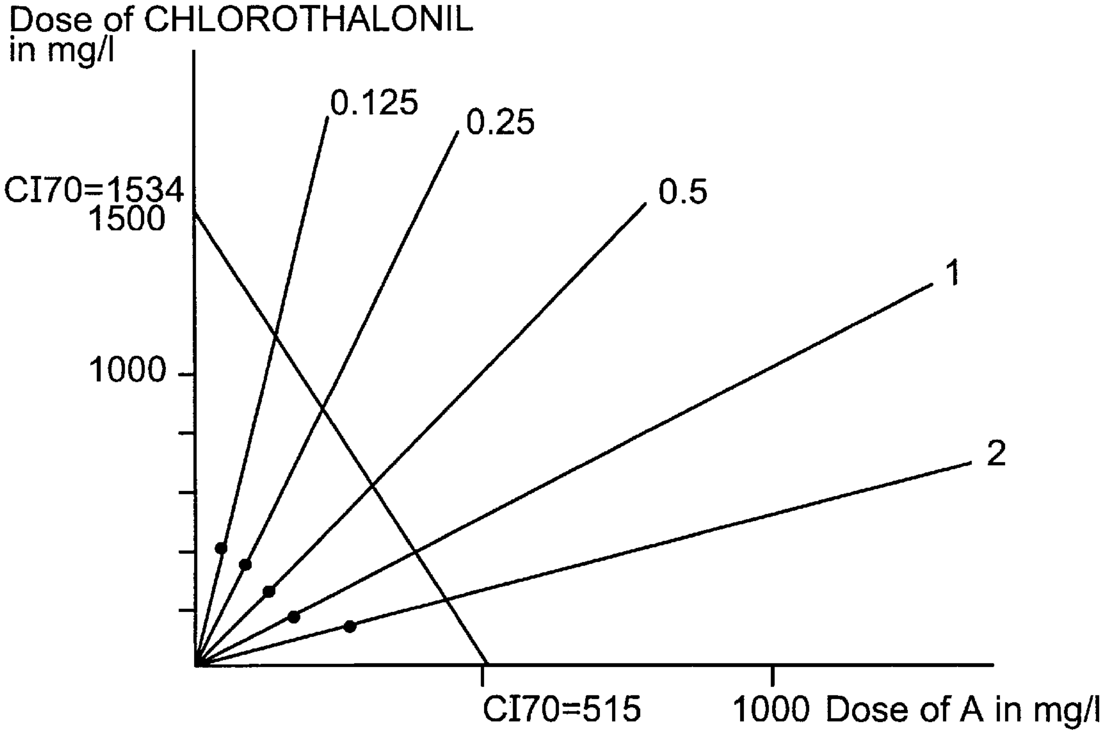
FIG. 7 is an $ED_{70}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and chlorothalonil as compound B.

The diagram of FIG. 7 is obtained which shows an arrangement of points similar to Example 5, characteristic of a synergy.

Example 9: In vivo trial of the combination of A with dimethomorph on *Plasmopara viticola* (vine downy mildew) by curative treatment at 48 hours Example 7 is repeated using as compound B dimethomorph; the A/B ratio is 0.25–0.5–1–2–4. The results corresponding to 90% destruction of the pest are presented.

Figure 8:
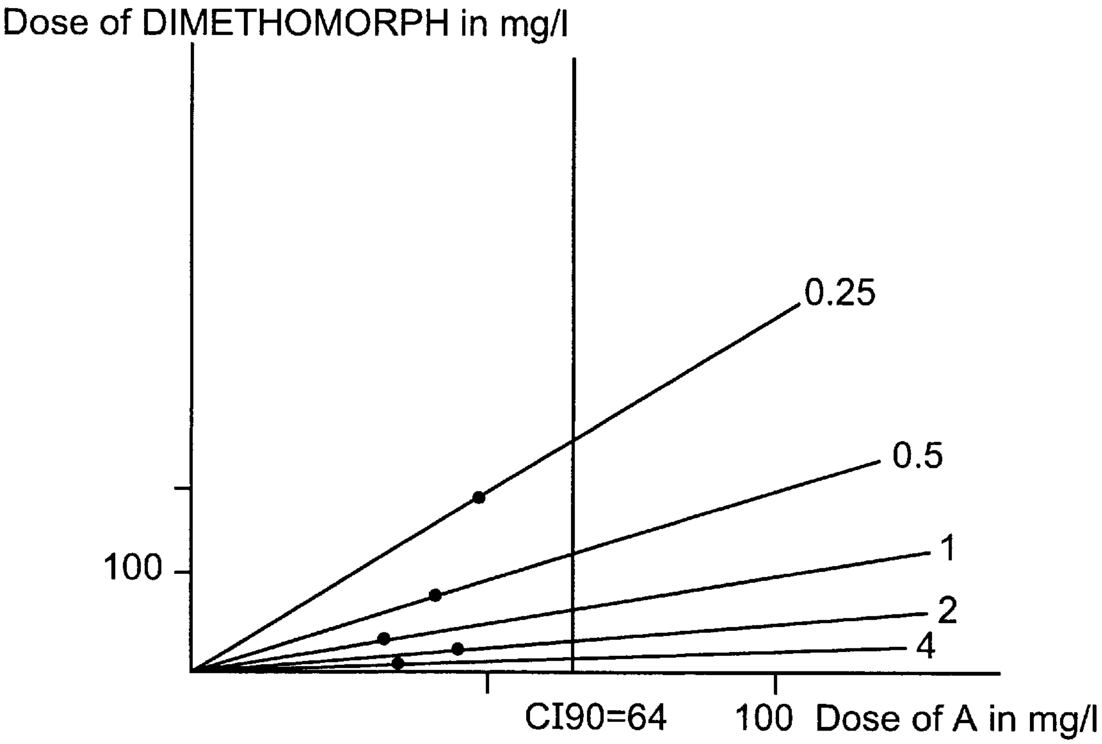
FIG. 8 is an $ED_{90}$ Tammes isobole plot for curative control of *Plasmopara viticola* in Chardonnay vine plants based on testing of combinations of (4S)-4-methyl-2-methylthio-4-phenyl-1-phenylamino-2-imidazolin-5-one as compound A and dimethomorph as compound B.

The diagram of FIG. 8 is obtained which shows an arrangement of points similar to Example 1, characteristic of a synergy.

Example 10: in vivo trial of the combination of A with metalaxyl on *Phytophthora infestans* (tomato blight, strain sensitive to phenylamides) by preventive treatment at 48 hours Example 1 is repeated using as compound B metalaxyl; the A/B ratio is 0.25–0.5–1–2. A strain sensitive to phenylamides is used.

Figure 9:
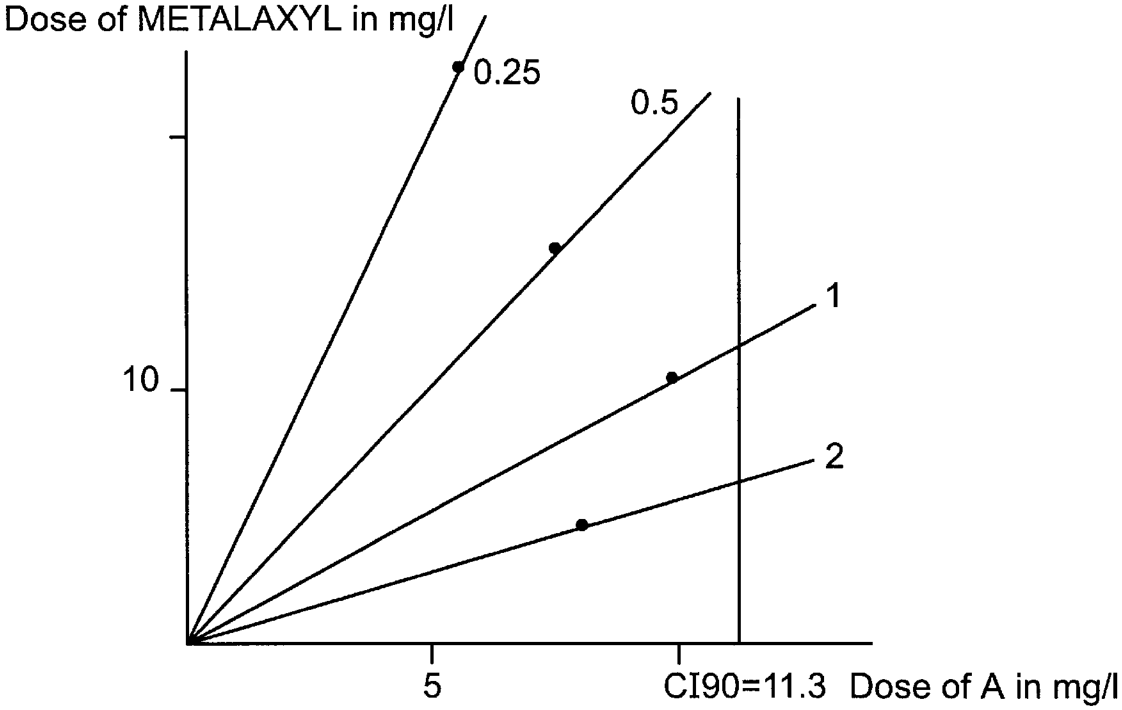
FIG. 9 is an $ED_{90}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and metalaxyl as compound B.

The diagram of FIG. 9 is obtained which shows an arrangement of the points similar to Example 1, and which is characteristic of a synergy.

Example 11: In vivo trial of the combination of A with metalaxyl on *Plasmopara viticola* (vine downy mildew) by preventive treatment at 24 hours Example 2 is repeated using as compound B metalaxyl; the A/B ratio is 2–4–8. The vine plants are contaminated 24 hours after having treated them with the suspension comprising the mixture of A and B.

Figure 10:
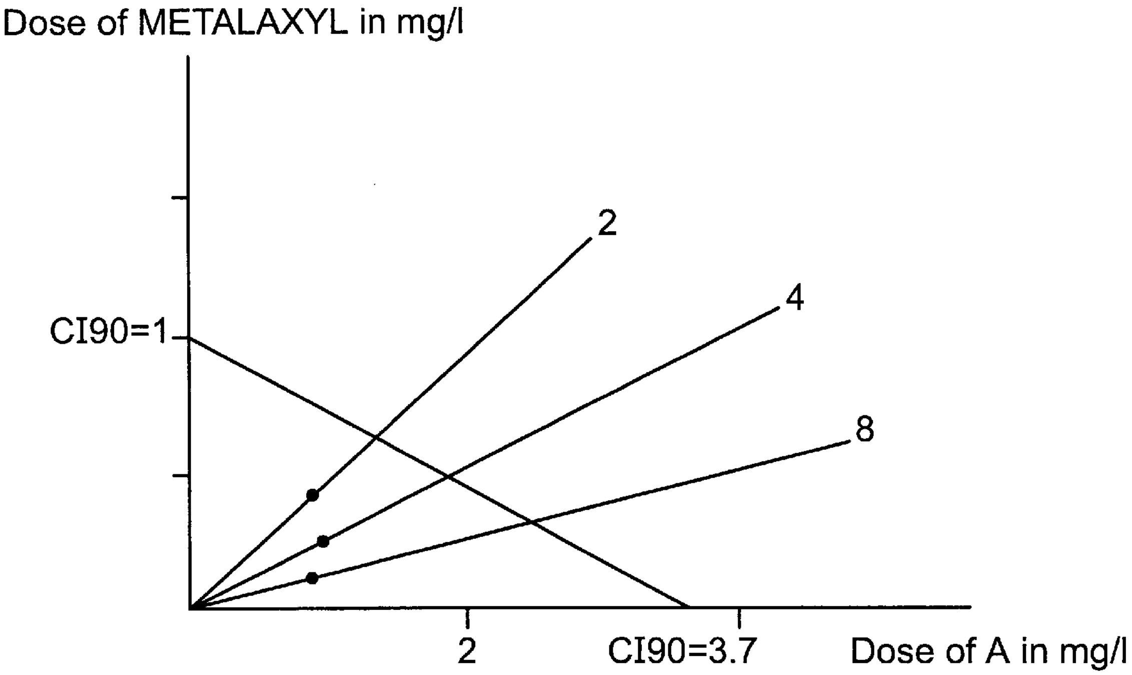
FIG. 10 is an $ED_{90}$ Tammes isobole plot for preventive control of *Plasmopara viticola* in Chardonnay vine plants based on testing of combinations of (4S)-4-methyl-2-methylthio-4-phenyl-1-phenylamino-2-imidazolin-5-one as compound A and metalaxyl as compound B.

The diagram of FIG. 10 is obtained which shows an arrangement of the points similar to Example 5, and which is characteristic of a synergy.

Example 12: In vivo trial of the combination of A with phosphorous acid on *Phytophthora infestans* (tomato blight) by preventive treatment at 48 hours Example 1 is repeated using as compound B phosphorous acid; the A/B ratio is 0.025–0.05–0.1–0.2–1. The results corresponding to 70% destruction of the pest are presented.

Figure 11:
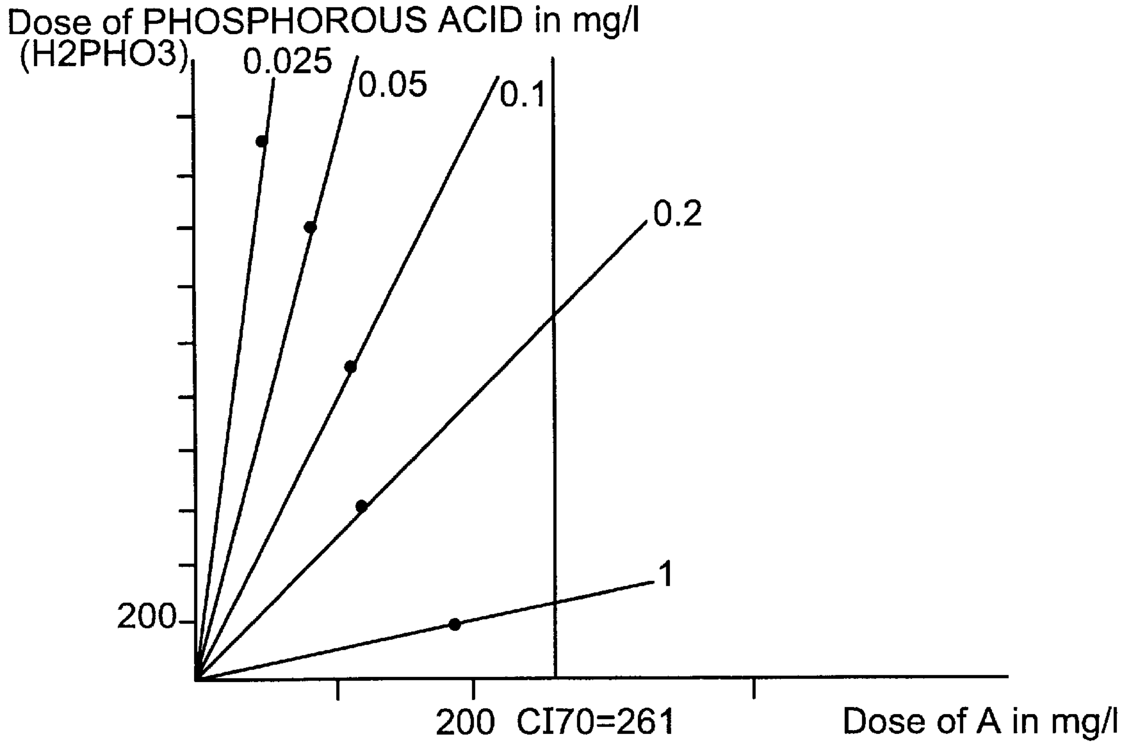
FIG. 11 is an $ED_{70}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and phosphorous acid as compound B.

The diagram of FIG. 11 is obtained which shows an arrangement of the points which is also similar to Example 1, and which is characteristic of a synergy.

Example 13: In vivo trial of the combination of A with the sodium salt of phosphorous acid on *Plasmopara viticola* (vine downy mildew) by preventive treatment at 24 hours Example 2 is repeated using as compound B the sodium salt of phosphorous acid; the A/B ratio is: 0.025–0.05–0.1. The vine plants are contaminated 24 hours after having treated them with the suspension comprising the mixture of A and B.

Figure 12:
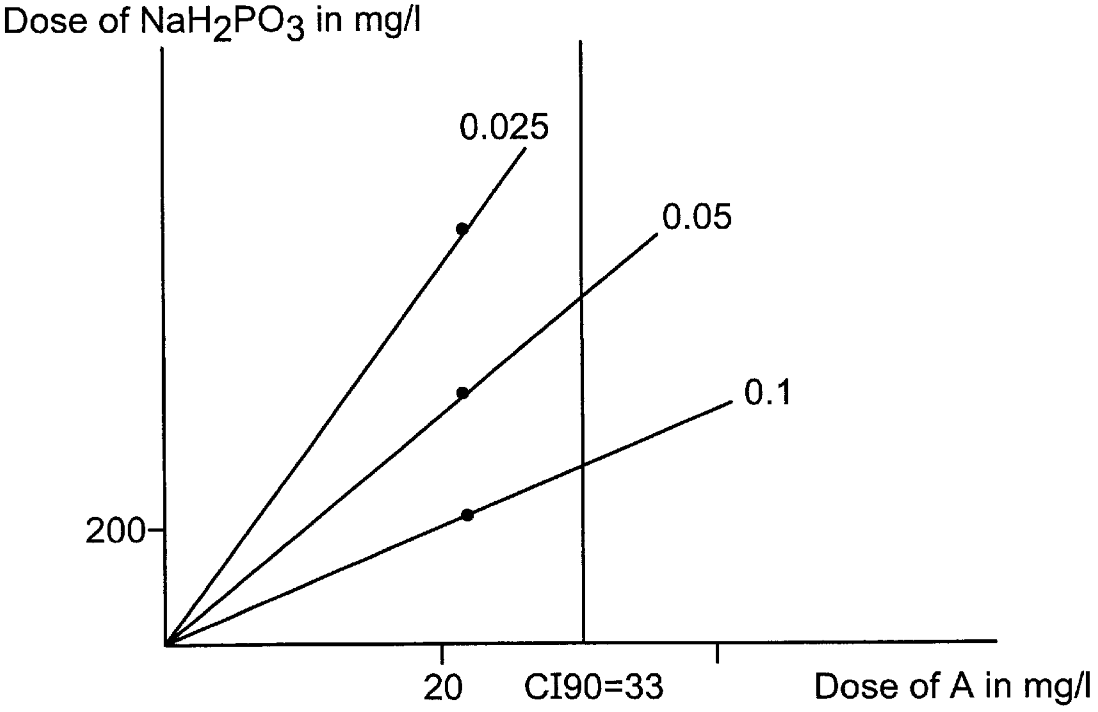
FIG. 12 is an $ED_{90}$ Tammes isobole plot for preventive control of *Plasmopara viticola* in Chardonnay vine plants based on testing of combinations of (4S)-4-methyl-2-methylthio-4-phenyl-1-phenylamino-2-imidazolin-5-one as compound A and the sodium salt of phosphorous acid as compound B.

The diagram of FIG. 12 is obtained which shows an arrangement of the points which is also similar to Example 2, and which is characteristic of a synergy.

Example 14: In vivo trial of the combination of A with cymoxanil on *Phytophthora infestans* (tomato blight) by preventive treatment at 48 hours Example 1 is repeated using as compound B cymoxanil; the A/B ratio is 0.25–0.5–1–2. The results corresponding to 70% destruction of the pest are presented.

Figure 13:
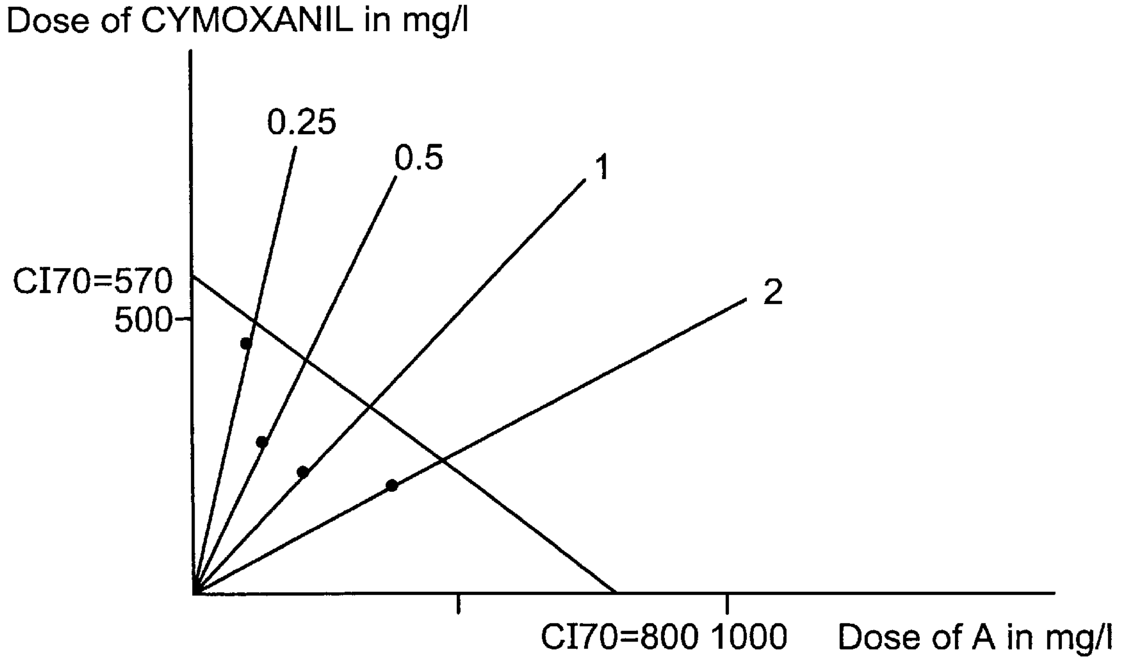
FIG. 13 is an $ED_{70}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and cymoxanil as compound B.

The diagram of FIG. 13 is obtained which shows an arrangement of the points similar to Example 5, and which is characteristic of a synergy.

Example 15: In vivo trial of the combination of A with cymoxanil on *Phytophthora infestans* (tomato blight) by curative treatment at 24 hours A 60 mg suspension is prepared comprising compounds A and B in a liquid mixture consisting of 0.3 ml of a surface-active agent (oleate of a polyoxyethylenated derivative of sorbitan) diluted 10% in water and of 60 ml of water.

Component B is cymoxanil; the A/B ratio is 0.25–0.5–1–2.

Tomato plants (Marmande variety) are cultivated in pots. When these plants are one month old (5 to 6-leaf stage, height 12 to 15 cm), they are contaminated by spraying using an aqueous *Phytophthora infestans* spore suspension (30,000 sp/$cm^3$).

At the end of 24 hours, these plants are contaminated by spraying the above suspension.

Next, the tomato plants are incubated for 7 days at about 20° C. in an atmosphere saturated with moisture.

The reading is made 7 days after the contamination, in comparison with the control plants.

The results obtained are presented in the form of points, corresponding to 90% destruction of the pest and are placed in a Tammes diagram which comprises, on the x-axis, the doses of cymoxanil expressed in mg/l and on the y-axis the doses of A also in mg/l.

Figure 14:
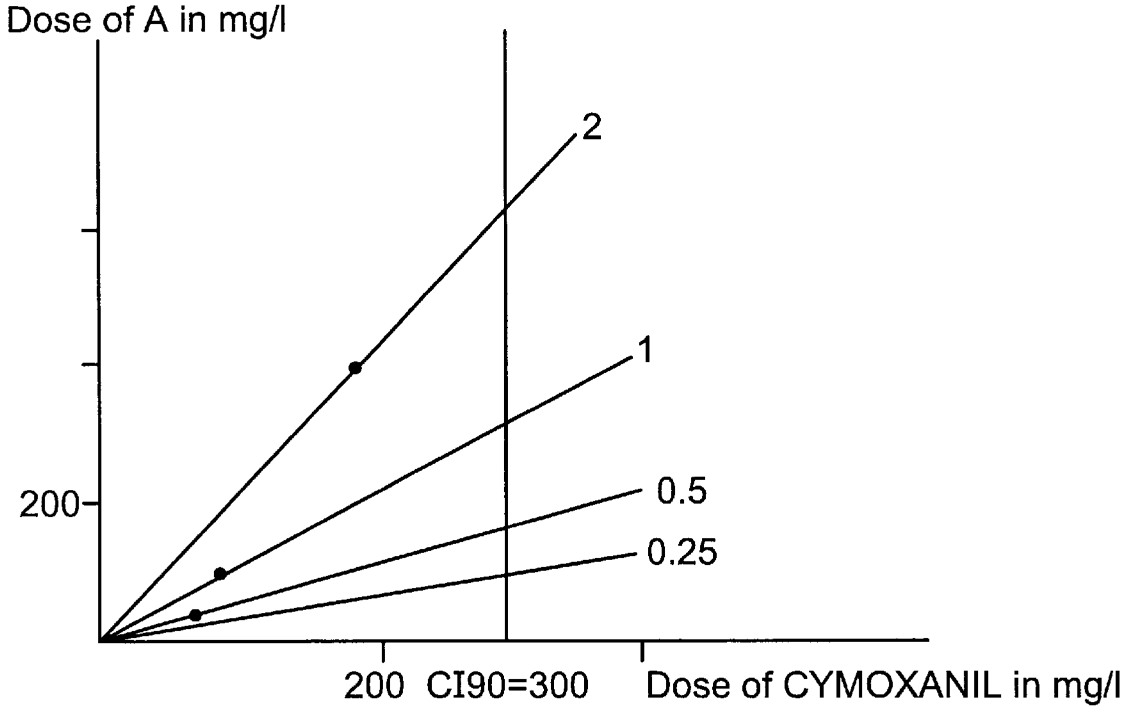
FIG. 14 is an $ED_{90}$ Tammes isobole plot for curative control of *Phytophthora infestans* in tomato plants based on testing of combinations of (4S)-4-methyl-2-methylthio-4-phenyl-1-phenylamino-2-imidazolin-5-one as compound A and cymoxanil as compound B.

The diagram of FIG. 14 is obtained in which the arrangement of the points indicates a one-sided effect characteristic of a synergy.

Example 16: In vivo trial of the combination of A with N-methyl-N-ethyl-2-(3,4-dimethoxyphenyl)-4-trifluoromethylbenzamide on *Plasmopara viticola* (vine downy mildew) by curative treatment at 48 hours Example 7 is repeated using as component B N-methyl-N-ethyl-2-(3,4-dimethoxyphenyl)-4-trifluoromethylbenzamide, using A/B ratios in the suspension for treating plants equal to 0.25–0.5–1–4.

Figure 15:
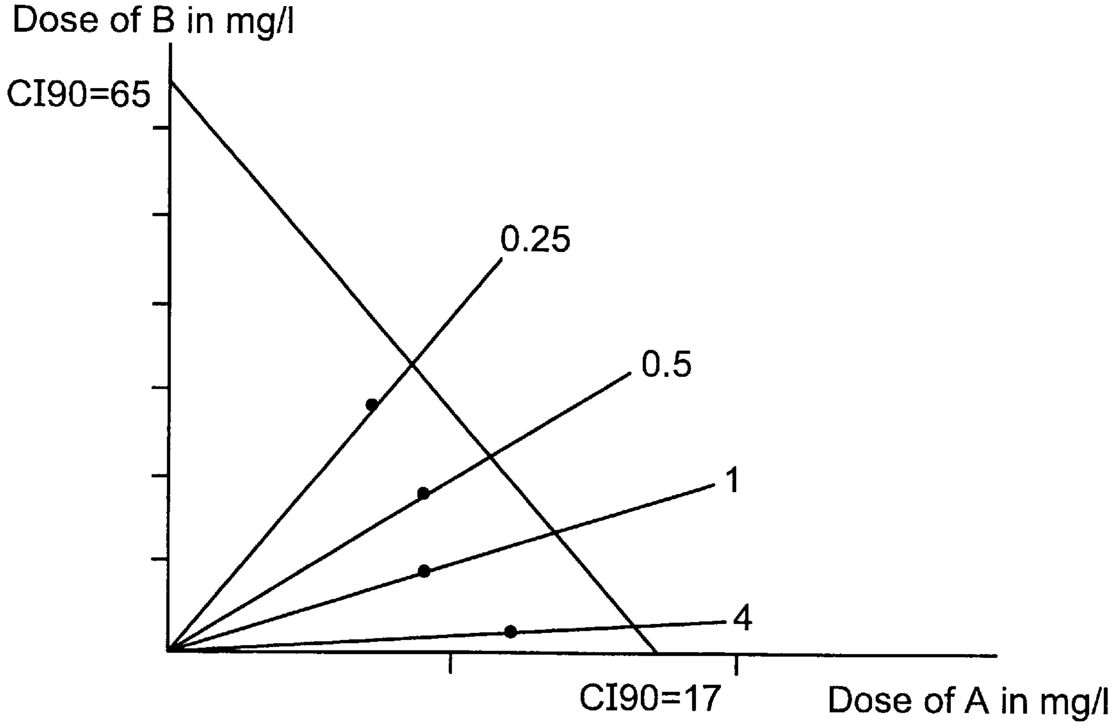
FIG. 15 is an $ED_{90}$ Tammes isobole plot for curative control of *Plasmopara viticola* in Chardonnay vine plants based on testing of combinations of (4S)-4-methyl-2-methylthio-4-phenyl-1-phenylamino-2-imidazolin-5-one as compound A and N-methyl-N-ethyl-2-(3,4-dimethoxyphenyl)-4-trifluoromethylbenzamide as compound B.

The diagram of FIG. 15 is obtained which shows an arrangement of the points similar to Example 5, and which is characteristic of a synergy.

Example 17: In vivo trial of the combination of A with methyl-(E)-methoxyimino[α-(o-tolyloxy)-o-tolyl]acetate on *Plasmopara viticola* (vine downy mildew) by preventive treatment at 24 hours Example 2 is repeated using as component B methyl-(E)-methoxyimino[α-(o-tolyloxy)-o-tolyl]acetate; using A/B ratios in the suspension for treating plants equal to 0.25–0.5–1. The vine plants are contaminated 24 hours after they have been treated with the suspension comprising the mixture of A and B.

Figure 16:
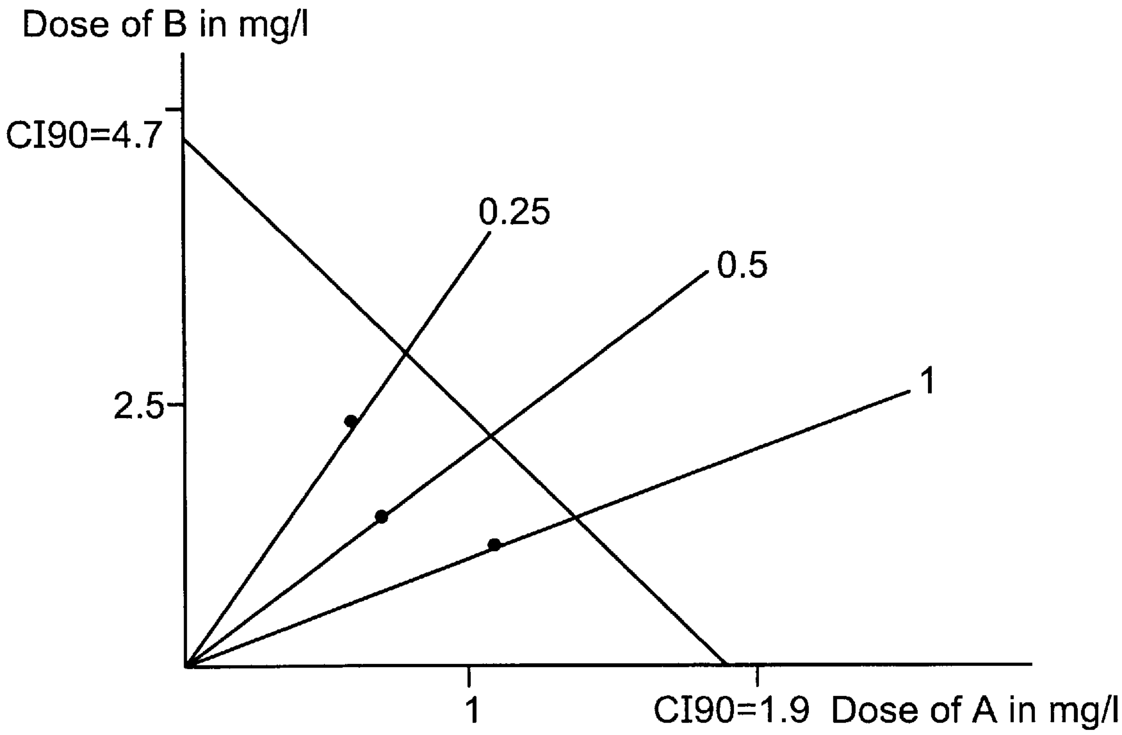
FIG. 16 is an $ED_{90}$ Tammes isobole plot for preventive control of *Plasmopara viticola* in Chardonnay vine plants based on testing of combinations of (4S)-4-methyl-2-methylthio-4-phenyl-1-phenylamino-2-imidazolin-5-one as compound A and methyl-(E)-methoxyimino[α-(o-tolyloxy)-o-tolyl]acetate as compound B.

The diagram of FIG. 16 is obtained which shows an arrangement of the points similar to Example 5, and which is characteristic of a synergy.

Example 18: In vivo trial of the combination of A with methyl-(E)-methoxyimino[α-(o-tolyloxy)-o-tolyl]acetate on *Plasmopara viticola* (vine downy mildew) by curative treatment at 48 hours Example 7 is repeated using as compound B methyl-(E)-methoxyimino[α-(o-tolyloxy)-o-tolyl]acetate; the A/B ratio is 0.25–0.5–1. The results corresponding to 90% destruction of the pest are presented.

Figure 17:
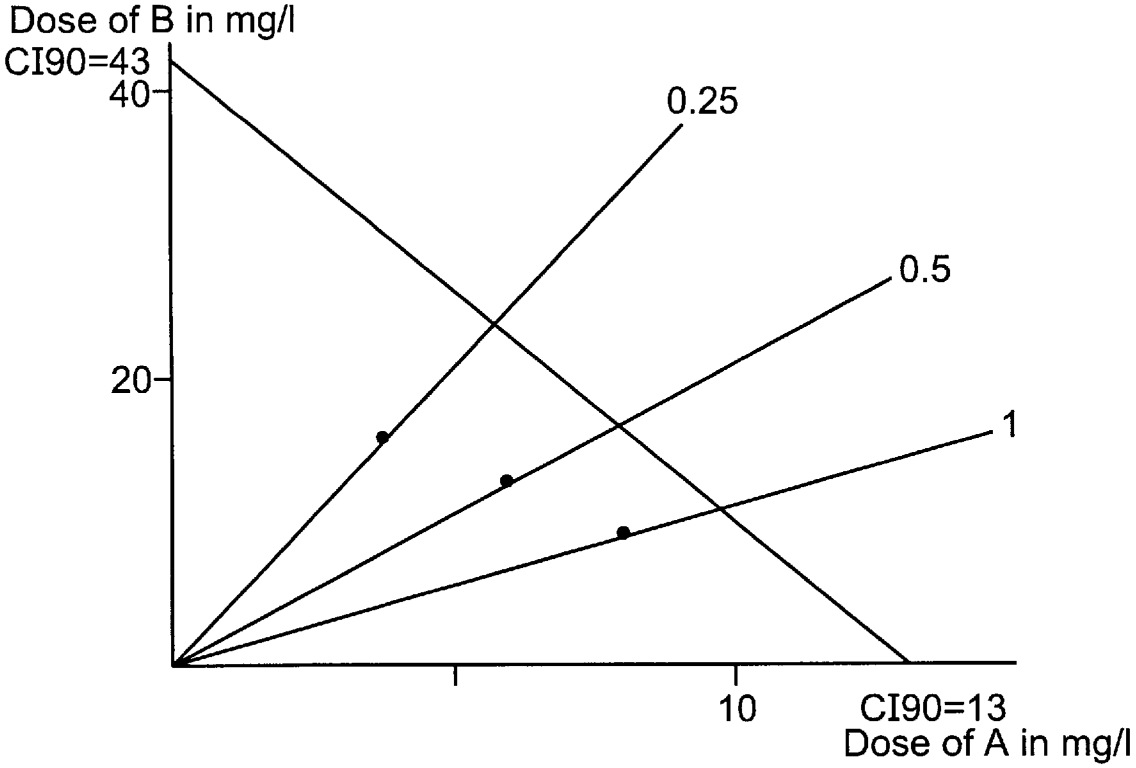
FIG. 17 is an $ED_{90}$ Tammes isobole plot for curative control of *Plasmopara viticola* in Chardonnay vine plants based on testing of combinations of (4S)-4-methyl-2-methylthio-4-phenyl-1-phenylamino-2-imidazolin-5-one as compound A and methyl-(E)-methoxyimino[α-(o-tolyloxy)-o-tolyl]acetate as compound B.

The diagram of FIG. 17 is obtained which shows an arrangement of the points similar to Example 5, and which is characteristic of a synergy.

Example 19: In vivo trial of the combination of A with methyl-(E)-2-{2-[6-(2-cyanophenoxy)pyrimidin-4-yloxy]phenyl}-3-methoxyacrylate on *Phytophthora infestans* (tomato blight) by preventive treatment at 48 hours Example 1 is repeated using as compound B methyl-(E)-2-{2-[6-(2-cyanophenoxy)pyrimidin-4-yloxy]phenyl}-3-methoxyacrylate; the A/B ratio is 0.25–0.5–1. The results corresponding to 90% destruction of the pest are presented.

Figure 18:
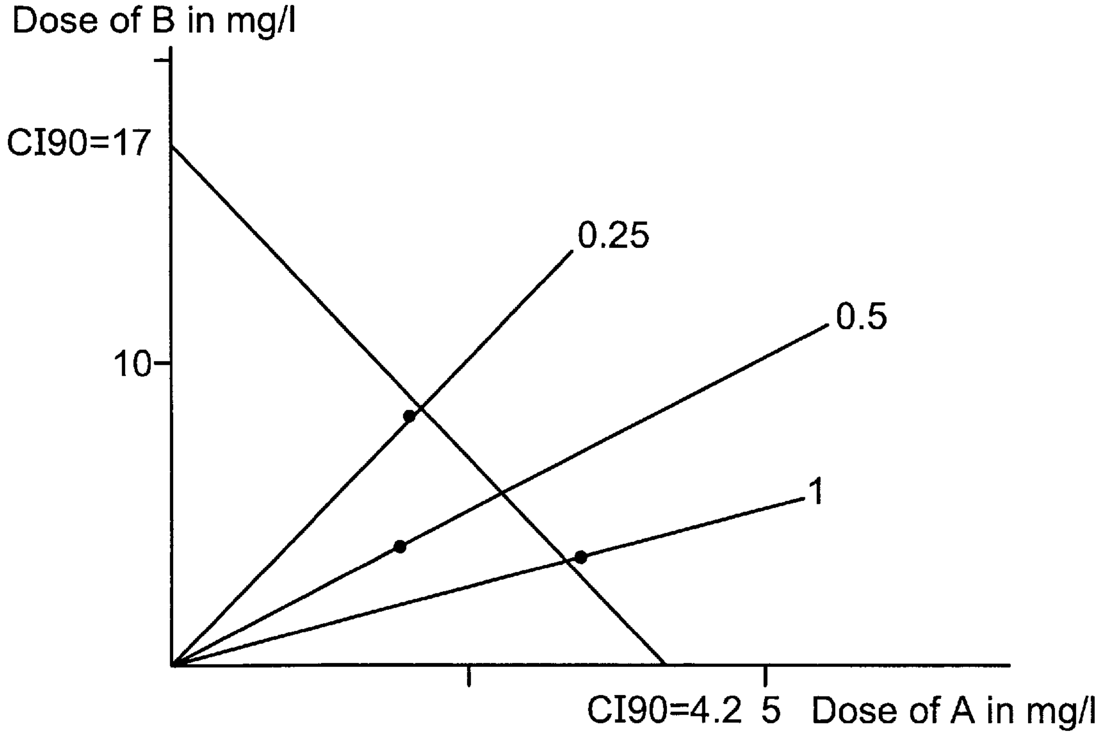
FIG. 18 is an $ED_{90}$ Tammes isobole plot for preventive control of *Phytophthora infestans* in tomato plants based on testing of combinations of (4S)-4-methyl-2-methylthio-4-phenyl-1-phenylamino-2-imidazolin-5-one as compound A and methyl-(E)-2-{2-[6-(2-cyanophenoxy)pyrimidin-4-yloxy]phenyl}-3-methoxyacrylate as compound B.

The diagram of FIG. 18 is obtained which shows an arrangement of the points similar to Example 5, and which is characteristic of a synergy.

Example 20: In vivo trial of the combination of A with fluazinam on *Phytophthora infestans* (potato blight, strain which in sensitive to phenylamides) by curative treatment at 24 hours Example 15 is repeated using potato plants (Bintje variety) and taking as compound B fluazinam; the A/B ratio is 0.11–0.33–1.

Figure 19:
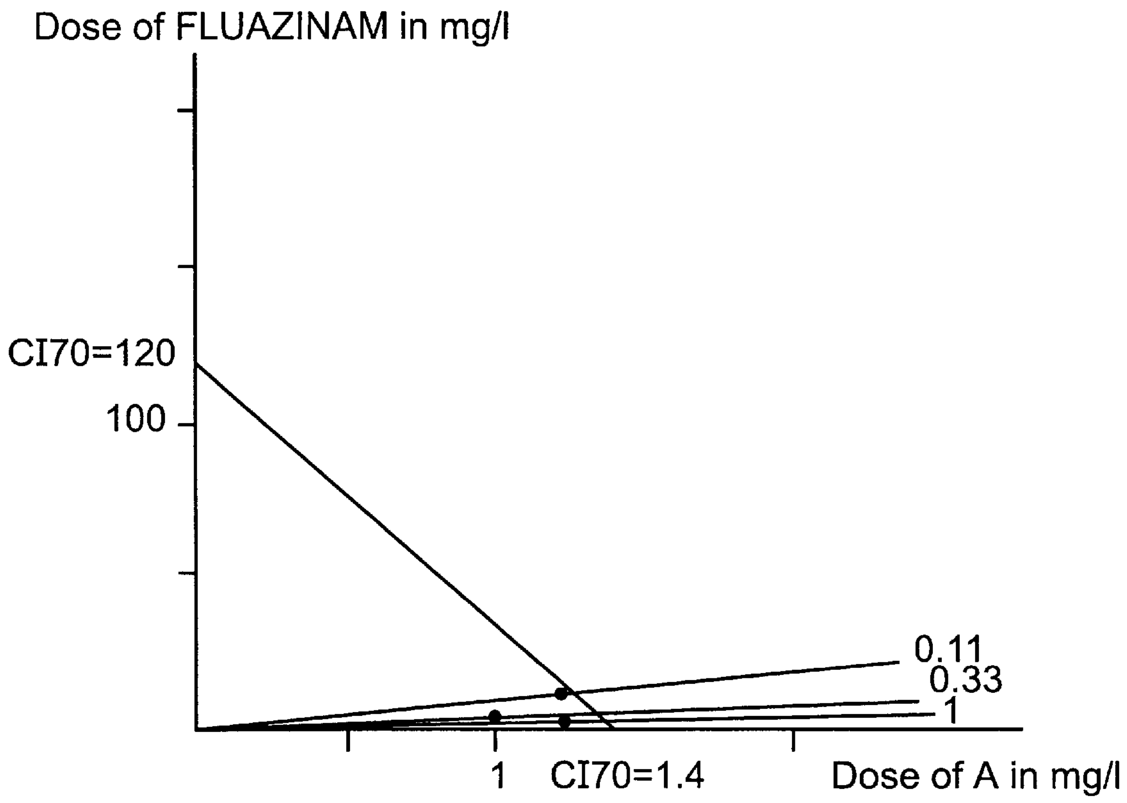
FIG. 19 is an $ED_{70}$ Tammes isobole plot for curative control of *Phytophthora infestans* in potato plants based on testing of combinations of (4S)-4-methyl-2-methylthio-4-phenyl-1-phenylamino-2-imidazolin-5-one as compound A and fluazinam as compound B.

The diagram of FIG. 19 is obtained.

Example 21: In vivo trial of the combination of A with epoxyconazole on *Septoria nodorum* (wheat septoria spot) by preventive treatment at 24 hours An aqueous concentrated suspension of A at 500 g/l is prepared.

Component B is epoxyconazole of which an aqueous concentrated suspension at 125 g/l is used.

Suspensions are then prepared comprising A and/or B diluted in water, so as to give the following values to the A/B ratio: 0.25–0.5. In all cases, a homogenous dilute suspension is obtained.

Wheat seeds of the Talent variety are cultivated in pots placed in a climatic cell in which the temperature is about 10° C. and the relative humidity about 70%. When these plants are 15 days old (size 8 to 10 cm), they are treated by applying a dilute suspension, an prepared above.

This application is made by means of a nozzle system which sprays the liquid by forming a cone whose angle at the vertex is between 70 and 110° C. Such a system is termed beam jet nozzle. This nozzle system is attached to a trolley which makes a translational movement relative to the pots placed on a fixed plate.

Such a system makes it possible to express the applied dose of A and/or B in g per hectare.

The experimental conditions are such that the volume of dilute aqueous suspension applied to the pots is 250 l/ha.

At the end of 24 hours, each plant is contaminated by spraying with an aqueous suspension of *Septoria nodorum* spores (500,000 sp/$cm^3$).

After this contamination, the wheat plants are incubated for 7 days at about 20° C.

The reading is made 7 days after the contamination, in comparison with the control plants contaminated with the pest, but which are not treated.

The results obtained are presented in the form of points corresponding to 90% destruction of the pest and which are placed in a Tammes diagram which comprises, on the x-axis, the dose of epoxyconazole expressed in g/ha and on the y-axis the dose of A also in g/ha.

Figure 20:
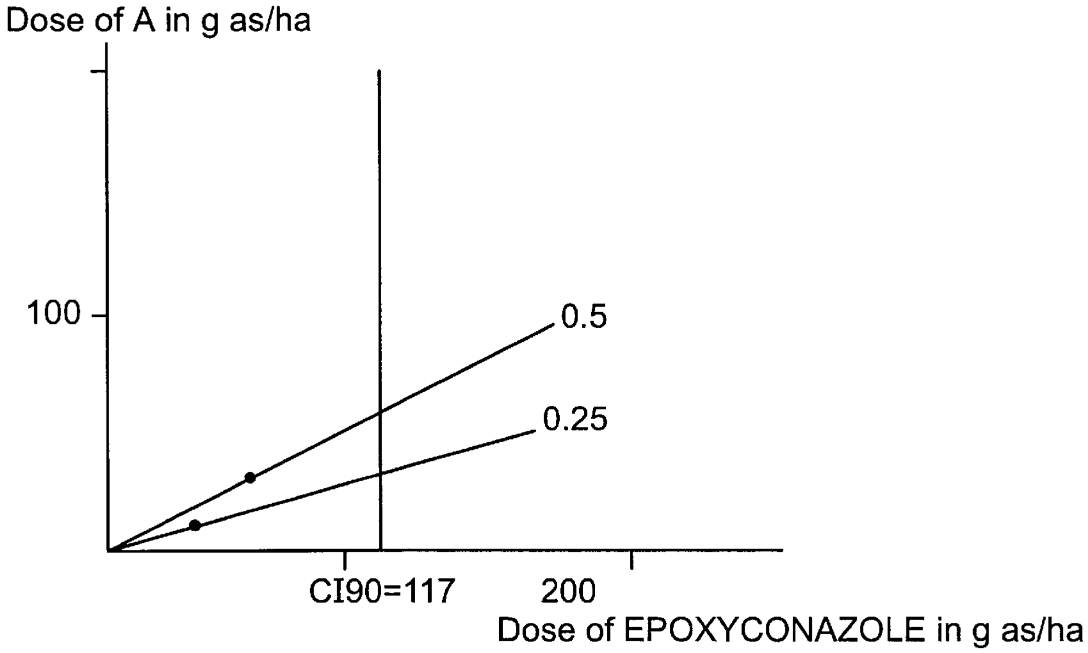
FIG. 20 is an $ED_{90}$ Tammes isobole plot for preventive control of *Septoria nodorum* in wheat plants based on testing of combinations of (4S)-4-methyl-2-methylthio-4-phenyl-1-phenylamino-2-imidazolin-5-one as compound A and epoxyconazole as compound B.

The diagram of FIG. 20 is obtained which shows an arrangement of points similar to Example 1 and which is characteristic of a synergy.

Example 22: In vivo trial of the combination of A with epoxyconazole on *Puccinia recondita* (wheat brown rust) by preventive treatment at 24 hours Example 21 is repeated by giving the following values to the A/B ratio: 0.1–0.2–1–2, and by carrying out the contamination with an aqueous suspension of *Puccinia recondita* spores (100,000 sp/$cm^3$).

The reading is made 10 days after the contamination, in comparison with the control plants contaminated with the pest, but not treated.

Figure 21:
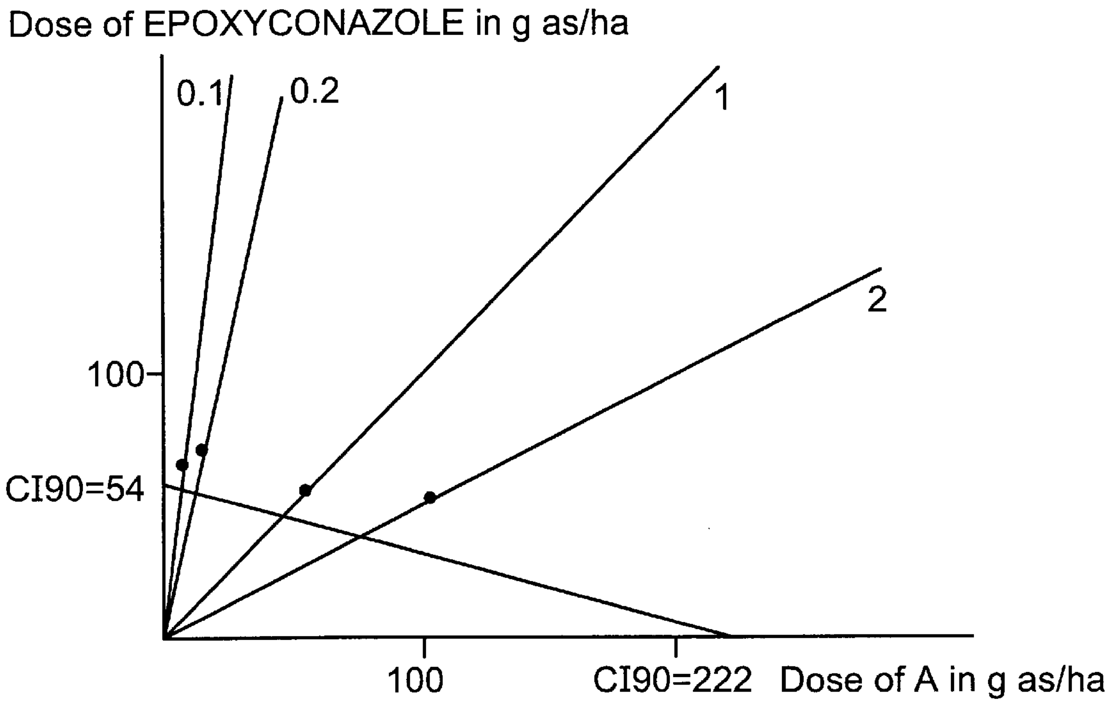
FIG. 21 is an $ED_{90}$ Tammes isobole plot for preventive control of *Puccinia recondita* in wheat plants based on testing of combinations of (4S)-4-methyl-2-methylthio-4-phenyl-1-phenylamino-2-imidazolin-5-one as compound A and epoxyconazole as compound B.

The diagram of FIG. 21 is obtained.

Example 23: In vivo trial of the combination of A with epoxyconazole on *Septoria tritici* (wheat septoria spot) preventive treatment at 24 hours Example 21 is repeated by giving the following values to the A/B ratio: 0.25–0.5–1 and by using wheat seeds of the Darius variety.

The contamination is carried out with an aqueous suspension of *Septoria tritici* spores (500,000 sp/$cm^3$) and the incubation is carried out at a temperature of 18° C. and of 15° C. at night for a period of 21 days.

The reading is made 21 days after the contamination, in comparison with the control plants contaminated with the pest, but not treated.

Figure 22:
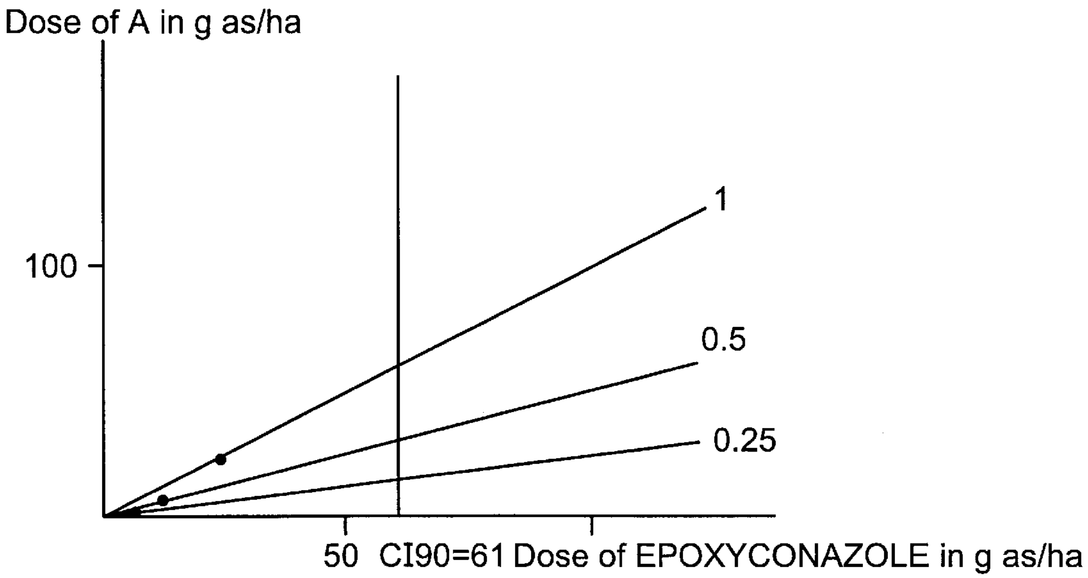
FIG. 22 is an $ED_{90}$ Tammes isobole plot for preventive control of *Septoria tritici* in wheat plants based on testing of combinations of (4S)-4-methyl-2-methylthio-4-phenyl-1-phenylamino-2-imidazolin-5-one as compound A and epoxyconazole as compound B.

The diagram of FIG. 22 is obtained which shows an arrangement of the points similar to Example 21, and which is characteristic of a synergy.

Example 24: In vivo trial of the combination of A with propiconazole on *Puccinia recondita* (wheat brown rust) by preventive treatment at 24 hours Example 22 is repeated by taking as compound B propiconazole of which a soluble concentrate at 125 g/l is used, and by giving the following values to the A/B ratio: 0.5–1–2.

The results corresponding to 70% destruction of the pest are presented.

Figure 23:
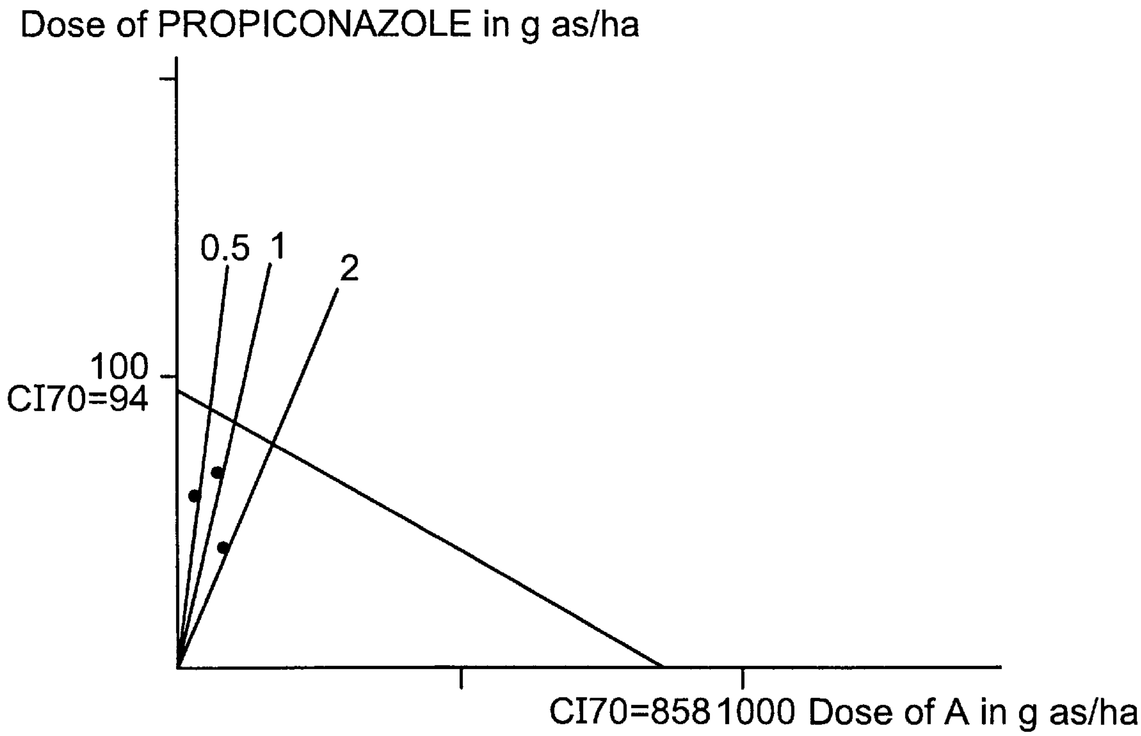
FIG. 23 is an $ED_{70}$ Tammes isobole plot for preventive control of *Puccinia recondita* in wheat plants based on testing of combinations of (4S)-4-methyl-2-methylthio-4-phenyl-1-phenylamino-2-imidazolin-5-one as compound A and propiconazole as compound B.

The diagram of FIG. 23 is obtained which shows an arrangement of the points similar to Example 5, and which is characteristic of a synergy.

Example 25: In vivo trial of the combination of A with propiconazole on *Septoria nodorum* (wheat septoria spot) by preventive treatment at 24 hours Example 21 is repeated by taking as compound B propiconazole of which a soluble concentrate at 125 g/l is used, and by giving the following values to the A/B ratio: 0.5–1–2.

Figure 24:
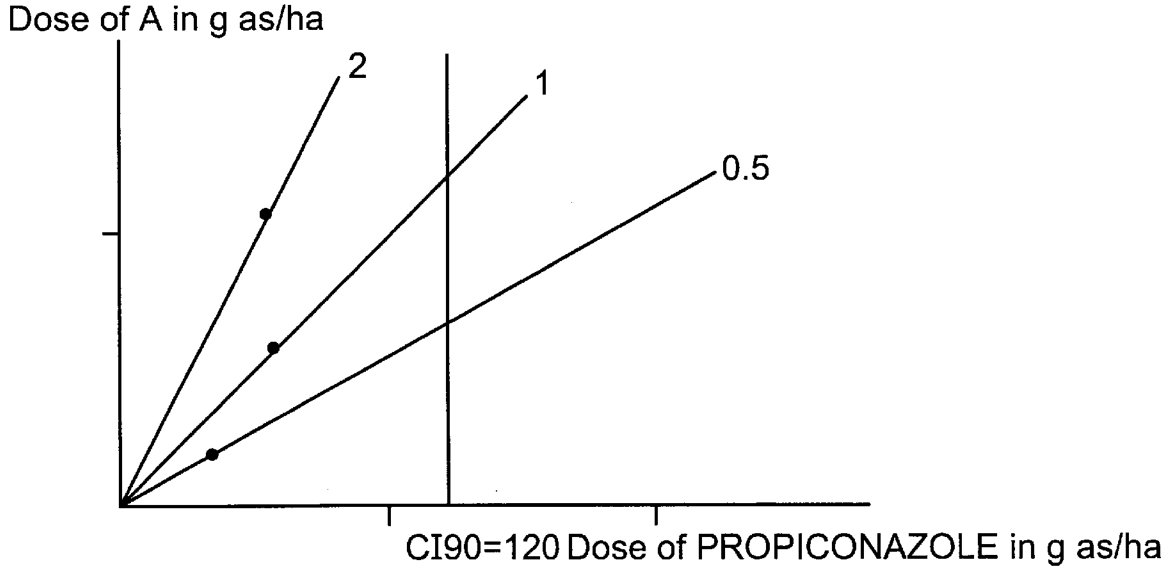
FIG. 24 is an $ED_{90}$ Tammes isobole plot for preventive control of *Septoria nodorum* in wheat plants based on testing of combinations of (4S)-4-methyl-2-methylthio-4-phenyl-1-phenylamino-2-imidazolin-5-one as compound A and propiconazole as compound B.

The diagram of FIG. 24 is obtained which shows an arrangement of the points characteristic of a synergy.

This example is also repeated by giving the following values to the A/B ratio: 0.1–0.2–1.

Figure 25:
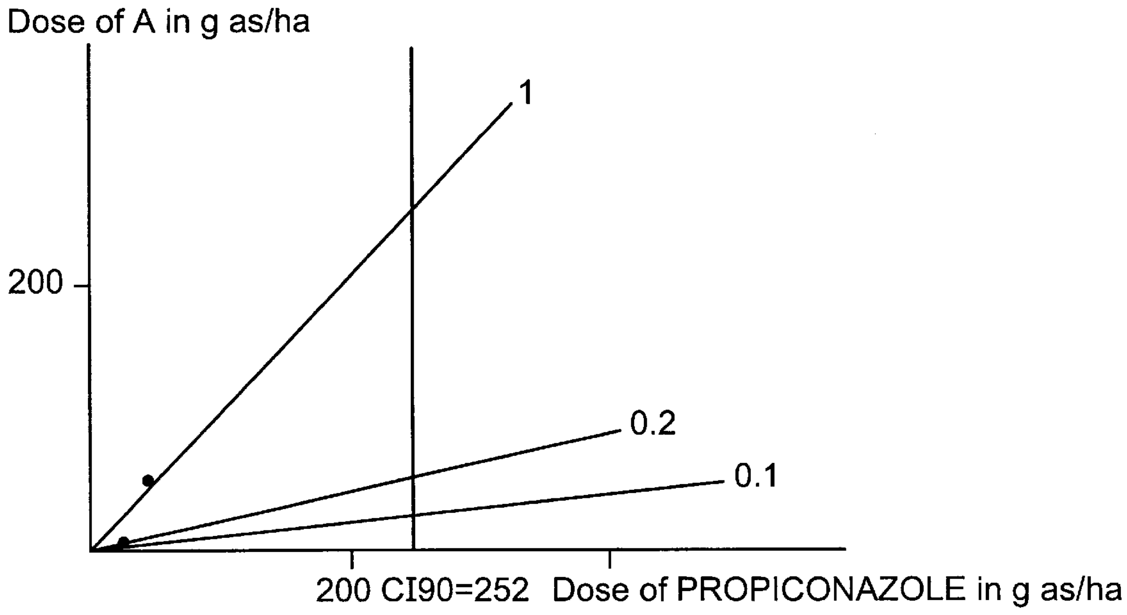
FIG. 25 is an $ED_{90}$ Tammes isobole plot for preventive control of *Septoria nodorum* in wheat plants based on testing of combinations of (4S)-4-methyl-2-methylthio-4-phenyl-1-phenylamino-2-imidazolin-5-one as compound A and propiconazole as compound B.

The diagram of FIG. 25 is obtained which shows an arrangement of the points characteristic of a synergy.

Example 26: In vivo trial of the combination of A with propiconazole on *Septoria tritici* (wheat septoria spot) by preventive treatment at 24 hours Example 23 is repeated by taking as compound B propiconazole of which a soluble concentrate at 125 g/l is used, and by giving the following values to the A/B ratio: 0.1–0.2–1.

The results corresponding to 90% destruction of the pest are presented.

Figure 26:
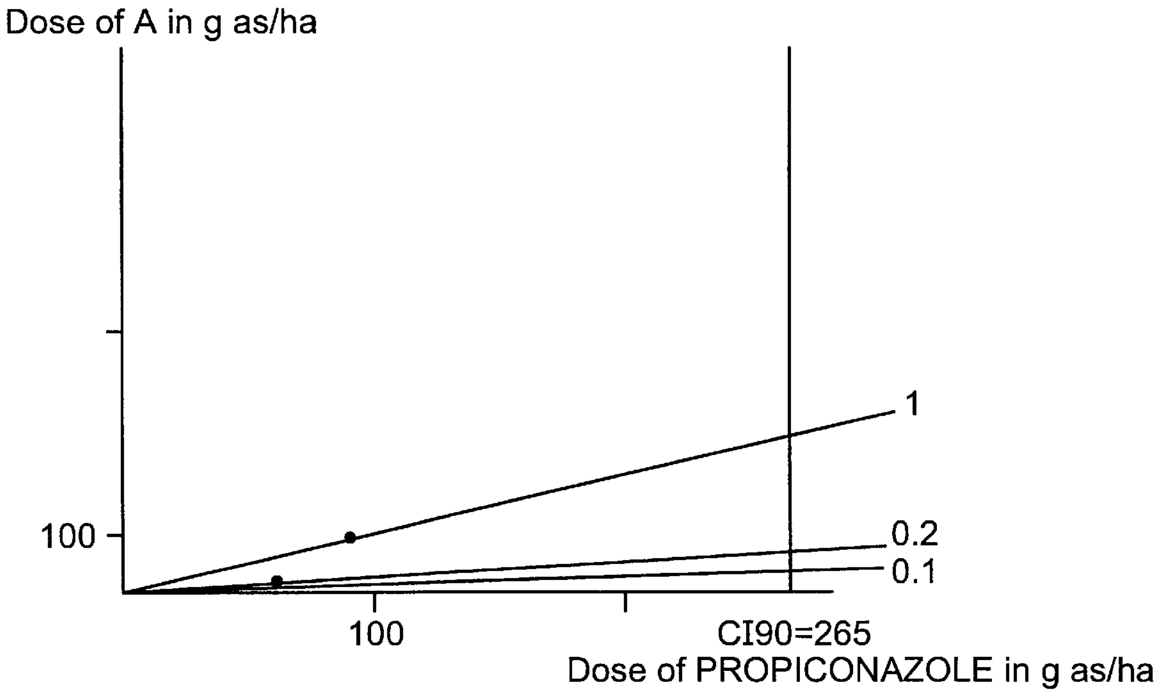
FIG. 26 is an $ED_{90}$ Tammes isobole plot for preventive control of *Septoria tritici* in wheat plants based on testing of combinations of (4S)-4-methyl-2-methylthio-4-phenyl-1-phenylamino-2-imidazolin-5-one as compound A and propiconazole as compound B.

The diagram of FIG. 26 is obtained which shows an arrangement of the points similar to Example 1, and which is characteristic of a synergy.

Example 27: In vivo trial of the combination of A with prochloraz on *Septoria nodorum* (wheat septoria spot) by preventive treatment at 24 hours Example 21 is repeated by taking as compound B prochloraz, and by preparing emulsifiable concentrates of A and B at 150 and 320 g/l, respectively, in a mixture of benzyl alcohol and an aromatic type solvent into which a surfactant pair consisting of castor oil ethoxylated with 33 moles of ethylene oxide and of calcium alkylarylsulphonate has been introduced.

The emulsions comprising A and/or B diluted in water are prepared so as to give the following values to the A/B ratio: 0.25–1–2. In all cases, a homogeneous dilute emulsion is also obtained.

Figure 27:
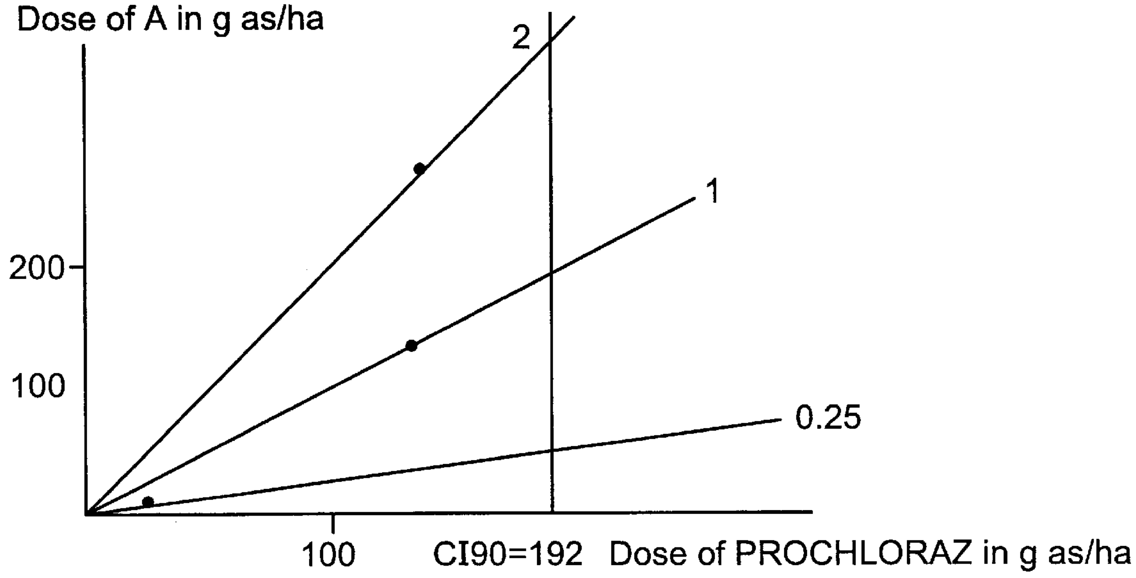
FIG. 27 is an $ED_{90}$ Tammes isobole plot for preventive control of *Septoria nodorum* in wheat plants based on testing of combinations of (4S)-4-methyl-2-methylthio-4-phenyl-1-phenylamino-2-imidazolin-5-one as compound A and prochloraz as compound B.

The diagram of FIG. 27 in obtained which shows an arrangement of the points characteristic of a synergy.

Figure 28:
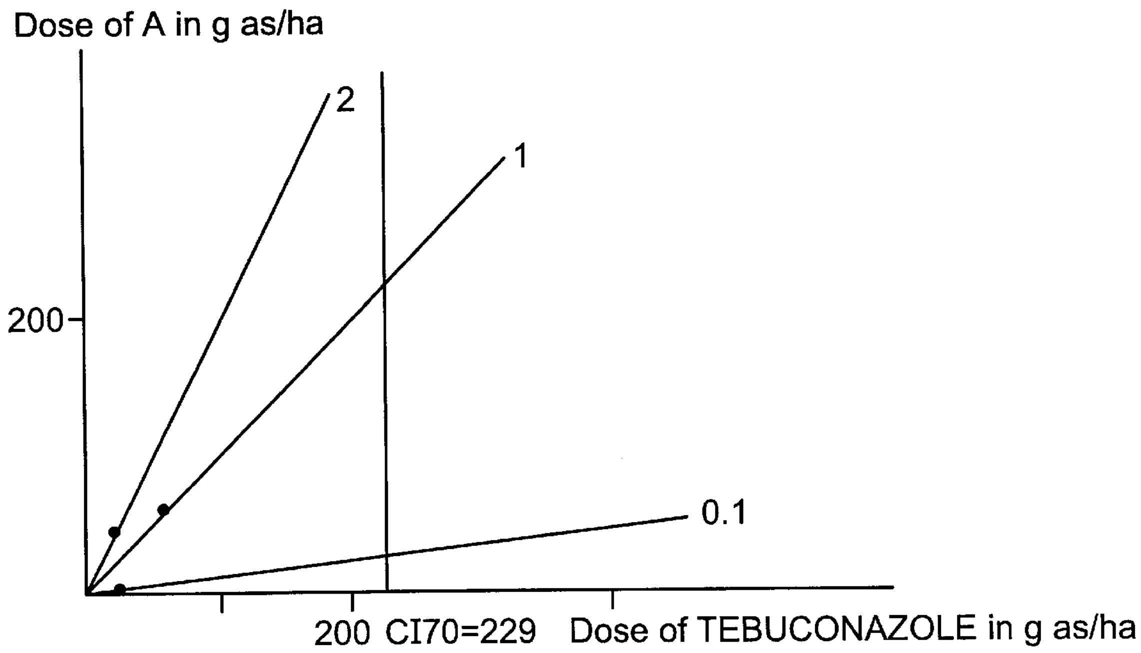
FIG. 28 is an $ED_{70}$ Tammes isobole plot for preventive control of *Septoria nodorum* in wheat plants based on testing of combinations of (4S)-4-methyl-2-methylthio-4-phenyl-1-phenylamino-2-imidazolin-5-one as compound A and tebuconazole as compound B.

Example 28: In vivo trial of the combination of A with tebuconazole on *Septoria nodorum* (wheat septoria spot) by preventive treatment at 24 hours Example 21 is repeated by taking as compound B tebuconazole of which a concentrated suspension at 25 g/l is used, and by giving the following values to the A/B ratio: 0.1–1–2. The dilute suspensions comprising A and/or B are homogeneous The diagram of FIG. 28 is obtained which shows an arrangement of the points characteristic of a synergy.

Example 29: In vivo trial of the combination of A with tebuconazole on *Puccinia recondita* (wheat brown rust) by preventive treatment at 24 hours Example 22 is repeated by taking as compound B tebuconazole of which a concentrated suspension at 25 g/l is used, and by giving the following values to the A/B ratio: 0.1–0.2–1–2. The dilute suspensions comprising A and/or B are homogeneous.

Figure 29:
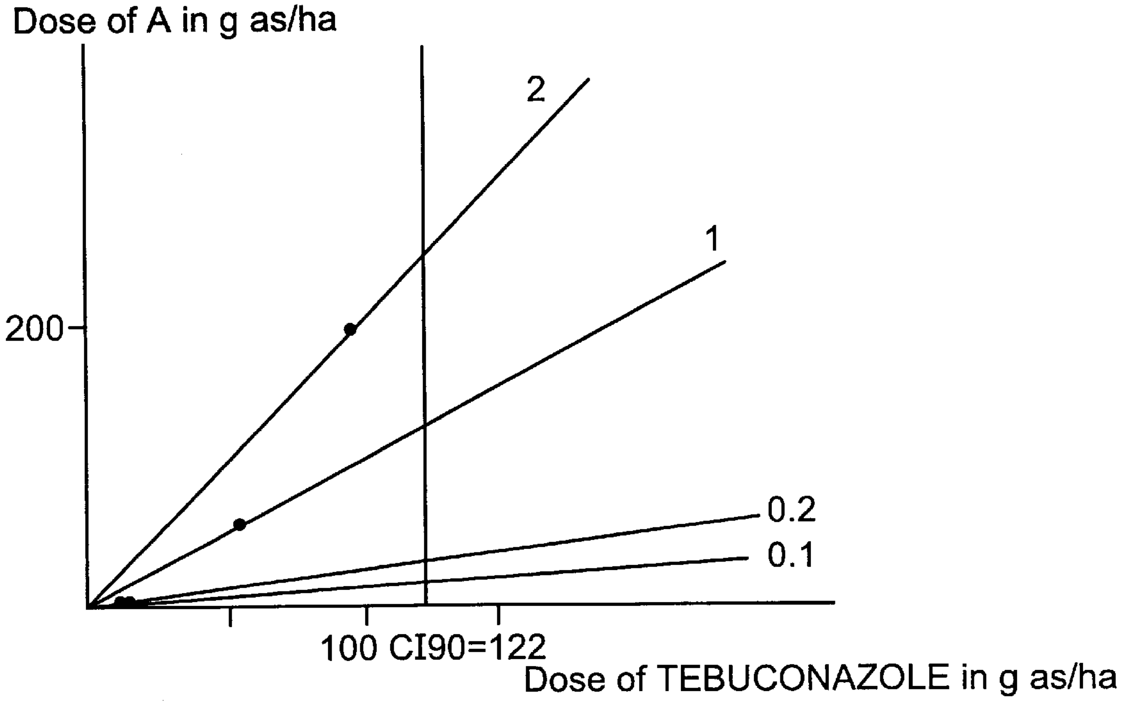
FIG. 29 is an $ED_{90}$ Tammes isobole plot for preventive control of *Puccinia recondita* in wheat plants based on testing of combinations of (4S)-4-methyl-2-methylthio-4-phenyl-1-phenylamino-2-imidazolin-5-one as is compound A and tebuconazole as compound B.

The diagram of FIG. 29 is obtained which shows an arrangement of the points characteristic of a synergy.

What is claimed is:

1. A fungicidal composition comprising: synergistic fungicidally effective amounts of (a) a compound A of formula (I):

(I)

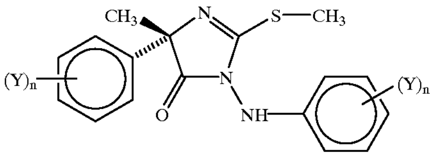

wherein n is an integer of 0 or 1, and Y is a fluorine atom, a chlorine atom, or a methyl radical; and (b) a fungicidal compound B which is an amide selected from the group consisting of: cymoxanil, metalaxyl, benalaxyl and oxadixyl, wherein compounds A and B are present in an A/B weight ratio ranges from 0.0005 to 50.

2. A fungicidal composition according to claim 1, wherein compound A is (4-S)-4-methyl-2-methylthio-4-phenyl-1-phenylamino-2-imidazolin-5-one.

3. A fungicidal composition according to claim 1, wherein compound B is cymoxanil.

4. A fungicidal composition according to claim 3, wherein the A/B weight ratio ranges from 0.05 to 4.

5. A fungicidal composition comprising synergistic fungicidally effective amounts of a compound A which is (4-S)-4-methyl-2-methylthio-4-phenyl-1-phenylamino-2-imidazolin-5-one, and a compound B which is cymoxanil, wherein compounds A and B are present in an A/B weight ratio ranges from 0.05 to 4.

6. A fungicidal composition according to claim 5, wherein the A/B ratio ranges from 0.2 to 4.

7. A fungicidal composition according to claim 6, wherein the A/B ratio ranges from 0.25 to 4.

8. A fungicidal composition according to claim 1, wherein compound B is oxadixyl.

9. A fungicidal composition according to claim 8, wherein the A/B weight ratio ranges from 0.5 to 30.

10. A fungicidal composition comprising synergistic fungicidally effective amounts of a compound A which is (4-S)-4-methyl-2-methylthio-4-phenyl-1-phenylamino-2-imidazolin-5-one, and a compound B which is oxadixyl, wherein compounds A and B are present in an A/B weight ratio ranges from 0.5 to 30.

11. A fungicidal composition according to claim 10, wherein the A/B ratio ranges from 0.5 to 10.

12. A fungicidal composition according to claim 1, further comprising at least one agriculturally acceptable solid or liquid carrier and at least one agriculturally acceptable surface-active agent.

13. A fungicidal composition according to claim 5, further comprising at least one agriculturally acceptable solid or liquid carrier and at least one agriculturally acceptable surface-active agent.

14. A fungicidal composition according to claim 10, further comprising at least one agriculturally acceptable solid or liquid carrier and at least one agriculturally acceptable surface-active agent.

15. A fungicidal composition according to claim 12, comprising from 5 to 40% by weight of said at least one agriculturally acceptable surface-active agent.

16. A fungicidal composition according to claim 13, comprising from 5 to 40% by weight of said at least one agriculturally acceptable surface-active agent.

17. A fungicidal composition according to claim 14, comprising from 5 to 40% by weight of said at least one agriculturally acceptable surface-active agent.

18. A fungicidal composition according to claim 11, comprising from 0.05 to 95% by weight of active substance.

19. A fungicidal composition according to claim 5, comprising from 0.05 to 95% by weight of active substance.

20. A fungicidal composition according to claim 10, comprising from 0.05 to 95% by weight of active substance.

21. A process for curatively or preventatively controlling phytopathogenic crop fungi, said method comprising applying to the aerial parts of crop plants a synergistic fungicidally effective amount of a composition according to claim 1.

22. A process for curatively or preventatively controlling phytopathogenic crop fungi, said method comprising applying to the aerial parts of crop plants a synergistic fungicidally effective amount of a composition according to claim 5.

23. A process for curatively or preventatively controlling phytopathogenic crop fungi, said method comprising applying to the aerial parts of crop plants a synergistic fungicidally effective amount of a composition according to claim 10.

24. A process according to claim 21, wherein from 10 to 5,000 g/ha of said composition is applied to said crop plants.

25. A process according to claim 22, wherein from 10 to 5,000 g/ha of said composition is applied to said crop plants.

26. A process according to claim 23, wherein from 10 to 5,000 g/ha of said composition is applied to said crop plants.

* * * * *